(12) United States Patent
Klug et al.

(10) Patent No.: US 11,110,121 B2
(45) Date of Patent: Sep. 7, 2021

(54) COMPOSITIONS COMPRISING HYDROGEN PEROXIDE OR HYDROGEN PEROXIDE DONOR SUBSTANCES

(75) Inventors: Peter Klug, Grossostheim (DE); Maurice Frederic Pilz, Frankfurt am Main (DE); Ute Back, Blankenbach (DE)

(73) Assignee: Clariant International Ltd., Muttenz (CH)

( * ) Notice: Subject to any disclaimer, the term of this patent is extended or adjusted under 35 U.S.C. 154(b) by 588 days.

(21) Appl. No.: 13/812,111

(22) PCT Filed: Jul. 15, 2011

(86) PCT No.: PCT/EP2011/003536
§ 371 (c)(1),
(2), (4) Date: Mar. 25, 2013

(87) PCT Pub. No.: WO2012/019688
PCT Pub. Date: Feb. 16, 2012

(65) Prior Publication Data
US 2014/0147402 A1    May 29, 2014

(30) Foreign Application Priority Data

Jul. 27, 2010  (DE) .................. 10 2010 032 371.3
Dec. 17, 2010  (DE) .................. 10 2010 054 918.5

(51) Int. Cl.
| | | |
|---|---|---|
| *A61K 33/40* | (2006.01) | |
| *A61K 8/22* | (2006.01) | |
| *A61Q 5/04* | (2006.01) | |
| *A61Q 5/08* | (2006.01) | |
| *A61Q 5/10* | (2006.01) | |
| *C01B 15/037* | (2006.01) | |
| *A61K 8/81* | (2006.01) | |
| *C11D 3/37* | (2006.01) | |
| *C11D 7/32* | (2006.01) | |
| *C11D 3/28* | (2006.01) | |
| *C01B 15/08* | (2006.01) | |
| *C01B 15/12* | (2006.01) | |
| *C11D 3/39* | (2006.01) | |
| *A61K 8/49* | (2006.01) | |
| *C11D 3/395* | (2006.01) | |
| *A61Q 11/00* | (2006.01) | |

(52) U.S. Cl.
CPC ............... *A61K 33/40* (2013.01); *A61K 8/22* (2013.01); *A61K 8/4926* (2013.01); *A61K 8/8158* (2013.01); *A61Q 5/04* (2013.01); *A61Q 5/08* (2013.01); *A61Q 5/10* (2013.01); *C01B 15/037* (2013.01); *C01B 15/085* (2013.01); *C01B 15/123* (2013.01); *C11D 3/28* (2013.01); *C11D 3/3707* (2013.01); *C11D 3/378* (2013.01); *C11D 3/3784* (2013.01); *C11D 3/3947* (2013.01); *C11D 3/3951* (2013.01); *C11D 7/3281* (2013.01); *A61K 2800/52* (2013.01); *A61Q 11/00* (2013.01)

(58) Field of Classification Search
CPC ..... A61K 8/4926; A61K 8/8158; A61K 33/40
See application file for complete search history.

(56) References Cited

U.S. PATENT DOCUMENTS

| | | | | |
|---|---|---|---|---|
| 4,185,106 | A * | 1/1980 | Dittmar | ............... A61Q 5/006 424/DIG. 4 |
| 4,656,043 | A * | 4/1987 | Hawkins | .................. A61K 8/22 424/59 |
| 4,711,775 | A | 12/1987 | Dittmar | |
| 4,804,705 | A | 2/1989 | Pum et al. | |
| 4,854,333 | A * | 8/1989 | Inman | ...................... A61K 8/23 132/202 |
| 5,206,385 | A | 4/1993 | Login et al. | |
| 6,083,422 | A | 7/2000 | Ambuter et al. | |
| 6,180,118 | B1 | 1/2001 | Maubru | |
| 2004/0074015 | A1 | 4/2004 | Kravtchenko et al. | |
| 2004/0081672 | A1* | 4/2004 | Gupta | ................... A61K 8/675 424/401 |
| 2004/0109838 | A1* | 6/2004 | Morschhuser | ....... A61K 8/8158 424/70.16 |
| 2005/0191263 | A1* | 9/2005 | Ueyama | ................ A61K 8/362 424/70.12 |
| 2006/0009371 | A1 | 1/2006 | Wang et al. | |
| 2006/0135382 | A1* | 6/2006 | Molenda | .................. A61K 8/37 510/119 |
| 2011/0003010 | A1 | 1/2011 | Klug et al. | |

(Continued)

FOREIGN PATENT DOCUMENTS

| | | | | |
|---|---|---|---|---|
| DE | WO 0185107 A1 * | 11/2001 | ........... A61K 8/4926 |
| DE | 102010054918 | | 6/2011 | |

(Continued)

OTHER PUBLICATIONS

English Abstract for DE102010054918, dated Jun. 30, 2011.

(Continued)

*Primary Examiner* — Kyle A Purdy
(74) *Attorney, Agent, or Firm* — Tod A. Waldrop

(57) ABSTRACT

A description is given of compositions comprising a) one or more substances selected from the group consisting of hydrogen peroxide and hydrogen peroxide donor substances, b) water, c) one or more polymers having thickening properties and d) one or more substances selected from the group consisting of hydroxypyridones and salts thereof. The compositions are notable more particularly for their advantageous shelf lives.

26 Claims, No Drawings

(56) References Cited

U.S. PATENT DOCUMENTS

| | | | |
|---|---|---|---|
| 2013/0236383 A1 | 9/2013 | Klug et al. | |
| 2013/0272984 A1 | 10/2013 | Klug et al. | |

FOREIGN PATENT DOCUMENTS

| | | |
|---|---|---|
| EP | 0751213 | 1/1997 |
| EP | 0 829 258 | 3/1998 |
| EP | 1 347 736 | 7/2002 |
| FR | 2 804 863 | 8/2001 |
| WO | 199821299 | 5/1998 |
| WO | 199953006 | 10/1999 |
| WO | 2002051369 | 7/2002 |
| WO | 2002051961 | 7/2002 |
| WO | WO 02/051369 | 7/2002 |
| WO | WO 02/051961 | 7/2002 |
| WO | WO 2009/015856 | 2/2009 |
| WO | 2012019688 | 2/2012 |

OTHER PUBLICATIONS

English Abstract for FR 2 804 863, dated Aug. 17, 2001.
Karlheinz Schrader, Andreas Domsch, Cosmetology—Theory and Practice, vol. II, Verlag für chemische Industrie, Augsburg, 2005, pp. 114-115.
Karlheinz Schrader, Andreas Domsch, Cosmetology—Theory and Practice, vol. II, Verlag für chemische Industrie, Augsburg, 2005, p. 145.
International Search Report for PCT/EP2011/003537, dated Mar. 6, 2012.
International Preliminary Report on Patentability for PCT/EP2011/003537, dated Jan. 29, 2013.
International Search Report for PCT/EP2011/003536, dated Mar. 5, 2012.
International Preliminary Report on Patentability for PCT/EP2011/003536, dated Feb. 14, 2013.
International Search Report for PCT/EP2011/006277, dated Mar. 5, 2012.
International Preliminary Report on Patentability for PCT/EP2011/006277, dated Jun. 20, 2013.
Technical Datasheet Sokalan, Jan. 1999. (6 pages).
Technical Report from Procter & Gamble, Nigel Somerville-Roberts, Mar. 2017. (2 pages).

* cited by examiner

COMPOSITIONS COMPRISING HYDROGEN PEROXIDE OR HYDROGEN PEROXIDE DONOR SUBSTANCES

The present invention relates to compositions comprising hydrogen peroxide or hydrogen peroxide-releasing substances.

Aqueous compositions comprising hydrogen peroxide are utilized in various applications. They are used in cosmetic compositions, for example as a bleach composition for hair, as a developer component in hair dyes, but also as a component for hair setting in permanent wave formulations. Further applications are, for example, tooth bleaching compositions. In industrial cleaning and in domestic cleaning too, acidic, hydrogen peroxide-containing compositions are present in cleaner formulations.

Due to the low viscosity of aqueous hydrogen peroxide solutions, aqueous solutions are not always advantageous since the low viscosity does not allow them to be applied accurately, and can cause them to spatter or to run too quickly.

Even in the case of addition of polyacrylate thickeners, the protonation of the thickener polymer at acidic pH causes no thickening to be achieved (Karlheinz Schrader, Andreas Domsch, Cosmetology—Theory and Practice, Volume II, Verlag für chemische Industrie, Augsburg, 2005, pages 114-115).

In cosmetics, therefore, particularly 0/W emulsions comprising hydrogen peroxide have been used to date for hair coloring formulations (Karlheinz Schrader, Andreas Domsch, Cosmetology Theory and Practice, Volume II, Verlag für chemische Industrie, Augsburg, 2005, page 145), these having better applicability due to the higher viscosity of the emulsions. The viscosity is generated here by the micellar structure of the emulsion.

Polymer-thickened compositions comprising hydrogen peroxide are known from the literature (see, for example, U.S. Pat. No. 4,804,705 or EP 0 829 258). EP 0 829 258 describes thickened hydrogen peroxide formulations which have elevated stability through the use of poly(acryloyldimethyltaurate) polymers.

EP 1 347 736 describes oxidative compositions for hair treatment, these comprising an amphiphilic polymer based on a sulfonated polymer containing a hydrophobic group. This involves using stabilizers based on pyrophosphate, stannates, phenacetin or oxyquinoline, or combinations thereof.

For commercial use, the above technologies, however, do not have adequate storage stability to date in spite of improved stability. It is found in practice that, even in the course of storage at elevated temperature, the hydrogen peroxide content in the formulations does not decrease, but the viscosity of the formulation nevertheless declines, often drastically, within weeks.

There was therefore a need for polymer-thickened compositions which have long-term storage stability and comprise hydrogen peroxide and/or hydrogen peroxide-releasing substances.

It has now been found that, surprisingly, addition of small amounts of hydroxypyridones or salts thereof can significantly improve the storage stability of aqueous polymer-thickened compositions comprising one or more substances selected from the group consisting of hydrogen peroxide and hydrogen peroxide-releasing substances.

The invention thus provides compositions comprising
a) one or more substances selected from the group consisting of hydrogen peroxide and hydrogen peroxide-releasing substances,
b) water,
c) one or more polymers having thickening properties and
d) one or more substances selected from the group consisting of hydroxypyridones and salts thereof.

This gives, for example, gel compositions which, due to the presence of the polymeric thickener, no longer have the abovementioned disadvantages and have excellent applicability. Especially compositions with shear-diluting properties can be applied very efficiently.

It is thus possible, in the case of use of the hydrogen peroxide formulations as a component in alkaline hair coloring formulations, to better control both the mixing of the components and the viscosity after the mixing of developer and coupler. In addition, it is also possible through the control of the viscosity to better control the volatility of the ammonia and therefore also the speed of the dyeing operation.

Preferably, the one or more substances of component a) are selected from the group consisting of hydrogen peroxide, urea peroxide, perborates, persulfates and mixtures thereof. More preferably, the substance of component a) is hydrogen peroxide.

The one or more substances selected from the group consisting of hydrogen peroxide and hydrogen peroxide-releasing substances of component a) are present in the inventive compositions preferably in amounts of 0.5 to 20% by weight, more preferably in amounts of 1 to 10% by weight, especially preferably in amounts of 1.5 to 7% by weight and exceptionally preferably in amounts of 2 to 7% by weight, based on the total weight of the compositions. Among these, the substance of component a) is again preferably hydrogen peroxide, which is present in the inventive compositions preferably in amounts of 0.5 to 20% by weight, more preferably in amounts of 1 to 10% by weight, especially preferably in amounts of 1.5 to 7% by weight and exceptionally preferably in amounts of 2 to 7% by weight, based on the total weight of the compositions.

In a preferred embodiment of the invention, the water (component b)) is present in the inventive compositions in an amount of 40% by weight or more and preferably in an amount of 50% by weight or more, based on the total weight of the compositions.

Polymers having thickening properties of component c) are, in the context of the present invention, preferably polymeric materials which have a molecular weight above 5000 g/mol and are suitable for significantly thickening a composition comprising one or more substances selected from the group consisting of hydrogen peroxide and hydrogen peroxide-releasing substances with use amounts of the polymer of 30% by weight or less, preferably of 10% by weight or less, more preferably of 6% by weight or less and especially preferably of 3% by weight or less, based on the total weight of the composition. This thickening is preferably such that the viscosity of the composition in mPas at 20° C. is increased by 30% or more with the abovementioned amounts of the polymers. Preference is given to polymers which exhibit thickening performance at a pH of <pH 7, preferably <pH 5, since hydrogen peroxide is particularly stable under these conditions.

Preferably, the one or more polymers having thickening properties of component c) are selected from the group consisting of polymers having a C—C backbone (i.e. having a carbon skeleton which can preferably be obtained by polymerization of olefinically unsaturated compounds), biopolymers, modified biopolymers, associative thickeners and polyalkylene glycols. In an embodiment of the invention preferred among these, the one or more polymers having thickening properties of component c) are selected from the group consisting of polymers having a C—C backbone, biopolymers, modified biopolymers and associative thickeners.

In a particularly preferred embodiment of the invention, the one or more polymers having thickening properties of component c) are selected from polymers having a C—C backbone.

Polymers having thickening properties having a C—C backbone are especially polymers based on acrylic acid, methacrylic acid and esters thereof, acrylamides and derivatives thereof, polyvinyl alcohol and derivatives thereof.

Preference is given here to polyacrylamides, polyacrylates and modified polyacrylates as obtainable, for example, under the Carbomer® brand name.

More preferably, however, the one or more polymers having a C—C backbone are selected from partly or fully neutralized polymers containing sulfo groups.

These polymers may be crosslinked or uncrosslinked. Particular preference is given to polymers based on acrylamidomethylpropanesulfonic acid (AMPS®, Lubrizol). These polymers, even at pH values of 7 or less, exhibit good thickening performance and are therefore particularly suitable for thickening of hydrogen peroxide solutions because hydrogen peroxide exhibits maximum stability at a pH of 3-5.

Especially preferably, the one or more partly or fully neutralized polymers containing sulfo groups are selected from the group consisting of homo- or copolymers of acrylamidomethylpropanesulfonic acid and salts thereof.

Among the polymers just mentioned, preference is in turn given to polymers having at least 20 mol % of units based on acrylamidomethylpropanesulfonic acid and/or salts thereof, and particular preference to polymers having at least 50 mol % of units based on acrylamidomethylpropanesulfonic acid and/or salts thereof, the mole figures relating in each case to the overall polymer.

In the case of the copolymers, as well as structural units based on acrylamidomethylpropanesulfonic acid and/or salts thereof, preferably one or more structural units based on the following comonomers are present in the copolymers: acrylic acid, methacrylic acid, acrylamide, dimethyl-acrylamide, vinylpyrrolidone (VP), hydroxyethyl acrylate, hydroxyethyl methacrylate, acrylic or methacrylic esters of ethoxylated alcohols RO—$(CH_2CH_2O)_m$H, in which R is an alkyl radical having 12 to 30 carbon atoms and m is a number from 3 to 30, and $CH_2$=CH—COO—$(CH_2CH_2$—COO$)_n$X in which n is a number from 0 to 10 and X is a counterion and is preferably $H^+$, $Na^+$ and/or $NH_4^+$.

The polymers selected from the group consisting of homo- or copolymers of acrylamidomethylpropanesulfonic acid and salts thereof may be crosslinked or uncrosslinked. In the case of crosslinking, they contain structural units based on monomers having 2 or more olefinic double bonds. In the case of crosslinking, preferably from 0.1 to 10 mol % of such structural units are present in the homo- or copolymers, based on the overall polymer.

If one or more structural units based on acrylamidomethylpropanesulfonic acid and/or salts thereof in the homo- or copolymers of acrylamidomethylpropanesulfonic acid and/or salts thereof have one or more counterions other than $H^+$, these other counterions are preferably selected from the group consisting of $Na^+$ and $NH_4^+$.

Suitable polymers are mentioned in publications including EP 0 816 403, EP 1 069 142, EP 1 116 733 and DE 10 2009 014877 (Clariant), EP 1 347 736 (L'Oreal) or EP 1 496 081 (Seppic). Examples include: Aristoflex® AVC (Ammonium Acryloyldimethyltaurate/VP Copolymer), Aristoflex® AVS (Sodium AcryloyldimethyltaurateNP Crosspolymer), Aristoflex® TAC (Ammonium Acryloyl Dimethyltaurate Carboxyethyl Acrylate Crosspolymer), Hostacerin® AMP5 (Ammonium Polyacryloyl-dimethyl Taurate), Aristoflex® HMB (Ammonium Acryloyldimethyl-taurate/Beheneth-25 Methacrylate Crosspolymer), Aristoflex® BLV (Ammonium Acryloyldimethyltaurate/Beheneth-25 Methacrylate Crosspolymer), Aristoflex® HMS (Ammonium Acryloyldimethyl-taurate/Steareth-25 Methacrylate Crosspolymer), Aristoflex® SNC (Ammonium Acryloyldimethyltaurate/Steareth-8 Methacrylate Copolymer), Aristoflex® LNC (Ammonium Acryloyldimethyltaurate/Laureth-7 Methacrylate Copolymer) or Sepinov® EMT 10 (Hydroxyethyl Acrylate/Sodium Acryloyldimethyl Taurate Copolymer), Sepigel® 305.

In a further particularly preferred embodiment of the invention, the one or more polymers having thickening properties of component c) are selected from the group consisting of biopolymers and modified biopolymers. These include polymers whose base skeleton is formed from sugar molecules or derivatives of sugar molecules (e.g. amino sugars, sugar acids, sugar esters). These polymers include cellulose ethers such as carboxyethyl cellulose or hydroxyethyl cellulose, starch and starch derivatives, natural gums such as xanthan gum, guar gum, hydroxypropyl guar, carrageenan, pectin, chitosan and chitosan derivatives. Likewise suitable are cationic biopolymers such as polyquaternium-10 (quaternized cellulose ether), cationic guar gums (Jaguar®, Rhodia) or cationic hydroxypropyl guars. Among the substances mentioned, preference is given to xanthan gum and cellulose ethers.

In a further particularly preferred embodiment of the invention, the one or more polymers having thickening properties of component c) are selected from associative thickeners. Associative thickeners are polymers which are based on polyethylene glycol and bear hydrophobic end groups, and can exhibit thickening performance either with or without additional surfactants. These are firstly ethoxylated/propoxylated polyols end-capped with fatty acids. Examples thereof are PEG-150-polyglyceryl-2-tristearate (Genapol® DAT 100, Clariant), PEG-150 distearate, PEG-150-pentaerythrityl tetrastearate (Crothix®, Croda) and PEG-120 methylglucose dioleate (Glucamate® DOE, Lubrizol).

In addition, this group includes etherified polyethylene glycols such as copolymers of ethylene oxide and dodecanediol, and polyurethanes based on polyethylene glycol. Examples include PEG-150/stearyl alcohol/SMDI copolymer (Aculyn® 46, Rohm & Haas) and PEG-150/decyl alcohol/SMDI copolymer (Aculyn® 44, Rohm & Haas).

Especially preferably, the one or more associative thickeners, however, are selected from phosphoric esters, preferably from neutral phosphoric esters. Examples of such phosphoric esters are given, for example, in publications WO 2009/015856, WO 2009/015857, WO 2009/015858, WO 2009/015859, WO 2009/015860 and WO 2009/095197. They have the advantage, among others, of sufficient hydrolysis stability at low pH. One example thereof is ceteareth-50 phosphate (Clariant).

In a further particularly preferred embodiment of the invention, the one or more polymers having thickening properties of component c) are selected from polyalkylene glycols. These are obtained by polymerizing 1,2-epoxides. Particular preference is given among these to the polyethylene glycols having 100 or more and preferably 100 to 100 000 monomer units, and to copolymers of ethylene oxide and propylene oxide having 100 or more and preferably 100 to 10 000 monomer units.

It is also possible to use mixtures of the abovementioned polymer types in the inventive compositions.

The one or more polymers having thickening properties of component c) are present in the inventive compositions preferably in amounts of 0.1 to 30% by weight, more preferably in amounts of 0.2 to 10% by weight, especially preferably in amounts of 0.3 to 6% by weight and exceptionally preferably in amounts of 0.3 to 3% by weight, based on the total weight of the compositions.

Preferably, the one or more substances of component d) are selected from compounds of the formula (I) and salts thereof

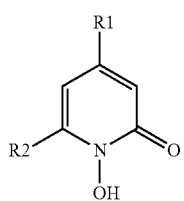

(I)

in which R1 is H or a $C_1$-$C_4$ alkyl radical and R2 is H, an unsubstituted or halogen-substituted, branched or unbranched $C_1$-$C_{20}$ alkyl radical, an unsubstituted or halogen-substituted $C_5$-$C_8$ cycloalkyl radical, an unsubstituted or halogen-substituted $C_8$-$C_{10}$ aryl radical or an unsubstituted or halogen-substituted, branched or unbranched $C_7$-$C_{20}$ aralkyl radical. In one embodiment of the invention which is preferred in this context, in the compounds of the formula (I), R1 is a $C_1$-$C_4$ alkyl radical and R2 is an unsubstituted or halogen-substituted, branched or unbranched $C_1$-$C_{20}$ alkyl radical, an unsubstituted or halogen-substituted $C_5$-$C_8$ cycloalkyl radical, an unsubstituted or halogen-substituted $C_6$-$C_{10}$ aryl radical or an unsubstituted or halogen-substituted, branched or unbranched $C_7$-$C_{20}$ aralkyl radical.

The R2 radicals are preferably not halogen-substituted.

In a preferred embodiment of the invention, the one or more compounds of component d) are present in the inventive compositions in the form of the acid (compounds of the formula (I)) or in the form of the alkali metal, alkaline earth metal or amine salts thereof, or salts thereof with polymeric counterions, for example polycationic polymers as counterions. In one embodiment of the invention which is preferred in this context, the one or more compounds of component d) are present in the inventive compositions in the form of the acid or in the form of the alkali metal, alkaline earth metal or amine salts thereof.

In a particularly preferred embodiment of the invention, R1 in the one or more compounds of the formula (I) or in the salts thereof is methyl, and R2 is cyclohexyl or 2,4,4-trimethylpentyl.

In a further particularly preferred embodiment of the invention, R1 and R2 in the one or more compounds of the formula (I) or in the salts thereof are each H.

More preferably, the compounds of the formula (I) are in the form of the alkanolamine salts thereof and especially preferably in the form of the monoethanolamine salts thereof. Examples of such salts are mentioned in DE 2234009.

Especially preferred are 4-methyl-6-(2,4,4-trimethylpentyl)-1-hydroxy-2-pyridone, monoethanolamine salt of 4-methyl-6-(2,4,4-trimethylpentyl)-1-hydroxy-2-pyridone (Octopirox®, Clariant), and 4-methyl-6-(cyclohexyl)-1-hydroxy-2-pyridone and the monoethanolamine salt of 4-methyl-6-(cyclohexyl)-1-hydroxy-2-pyridone (Ciclopirox®, Sanofi-Aventis).

These substances can be obtained by methods known from the literature; cf. the references cited in DE 2234009.

In the inventive compositions, the one or more substances of component d) are present in amounts of preferably 0.1 to 20 000 ppm (0.00001 to 2% by weight), more preferably in amounts of 0.5 to 1000 ppm (0.00005 to 0.1% by weight) and especially preferably in amounts of 1 to 100 ppm (0.0001 to 0.01% by weight), based on the total weight of the compositions.

The hydroxypyridones can be combined in the inventive compositions with further stabilizers. Further suitable stabilizers are, for example, polyphosphates and the alkali metal or alkaline earth metal salts thereof, alkali metal or alkaline earth metal stannates, phenacetin and the acid salts thereof, and oxyquinoline and the acid salts thereof. In general, the hydrogen peroxide solutions ready for delivery already comprise stabilizers, preferably in the form of polyphosphates.

The inventive compositions can be used as bleaching compositions for hair or teeth, as a bleaching component or developer for oxidative hair dyes or as a fixing component for permanent wave formulations and as a domestic cleaner. In addition, the inventive compositions can be used as stain removal gels for pretreatment of laundry, prewash sprays, stain removers, surface cleaners, toilet cleaners, multifunctional stain removal gels or bleaching gels. A further possible use is that of hair coloring compositions for prevention of bleaching damage in the course of hair coloring.

The viscosity of the inventive compositions is preferably 50-100 000 mPa·s at 20° C., more preferably 100-20 000 mPa·s at 20° C. and especially preferably 150-5000 mPa·s at 20° C. The viscosities are measured on the inventive compositions themselves with a Brookfield model DV II viscometer, at 20 revolutions/minute and 20° C. Spindles 1 to 7 from the RV spindle set are used. Under these measurement conditions, spindle 1 is selected for viscosities not exceeding 500 mPa·s, spindle 2 for viscosities not exceeding 1000 mPa·s, spindle 3 for viscosities not exceeding 5000 mPa·s, spindle 4 for viscosities not exceeding 10 000 mPa·s, spindle 5 for viscosities not exceeding 20 000 mPa·s, spindle 6 for viscosities not exceeding 50 000 mPa·s and spindle 7 for viscosities not exceeding 200 000 mPa·s.

In a preferred embodiment of the invention, the inventive compositions are oil-free compositions of gel-like consistency.

In a further preferred embodiment of the invention, the inventive compositions are emulsions. The emulsions are preferably oil-in-water emulsions or microemulsions.

The nonaqueous proportion of these emulsions, which is composed substantially of the emulsifier and the oil body, is typically 0.5 to 20.0% by weight and preferably 1.0 to 10.0% by weight, based on the total weight of the emulsions. It follows from this that the emulsions may contain 80.0 to 99.5% by weight and preferably 90.0 to 99.0% by weight of the aqueous phase, based on the total weight of the emulsions.

The inventive compositions may also comprise anionic, cationic, nonionic, ampholytic surfactants and/or betaine surfactants.

The total amount of the surfactants used in the inventive compositions is, based on the total weight of the compositions, preferably from 0.1 to 20% by weight, more preferably from 0.5 to 10.0% by weight and especially preferably from 1.0 to 5.0% by weight.

Preferred anionic surfactants are ($C_{10}$-$C_{22}$)-alkyl and alkylene carboxylates, alkyl ether carboxylates, fatty alcohol sulfates, fatty alcohol ether sulfates, alkylamide sulfates and sulfonates, fatty acid alkylamide polyglycol ether sulfates, alkanesulfonates and hydroxyalkanesulfonates, olefinsulfonates, acyl esters of isethionates, α-sulfo fatty acid esters, alkylbenzenesulfonates, alkylphenol glycol ether sulfonates, sulfosuccinates, sulfosuccinic monoesters and diesters, fatty alcohol phosphates, fatty alcohol ether phosphates, protein-fatty acid condensation products, alkyl monoglyceride sulfates and sulfonates, alkyl glyceride ether sulfonates, fatty acid methyl taurides, fatty acid sarcosinates, sulforicinoleates, acyl glutamates and acyl glycinates. These compounds and mixtures thereof are utilized in the form of the water-soluble or water-dispersible salts thereof, for example the sodium, potassium, magnesium, ammonium, mono-, di- and triethanolammonium, and analogous alkylammonium salts.

The amount of the anionic surfactants in the inventive compositions is preferably from 0.05 to 20.0% by weight, more preferably from 0.5 to 10.0% by weight and especially preferably from 1.0 to 5.0% by weight, based on the total weight of the compositions.

Preferred cationic surfactants are quaternary ammonium salts, such as di($C_8$-$C_{22}$)-alkyldimethylammonium chloride or bromide, preferably di($C_8$-$C_{22}$)-alkyldimethylammonium chloride or bromide; ($C_8$-$C_{22}$)-alkyl-dimethylethylammonium chloride or bromide; ($C_8$-$C_{22}$)-alkyltrimethylammonium chloride or bromide, preferably cetyltrimethylammonium chloride or bromide and ($C_8$-$C_{22}$)-alkyltrimethylammonium chloride or bromide; ($C_{10}$-$C_{24}$)-alkyldimethylbenzylammonium chloride or bromide, preferably ($C_{12}$-$C_{18}$)-alkyldinnethylbenzylammonium chloride, ($C_8$-$C_{22}$)-alkyl-dimethylhydroxyethylammonium chloride, phosphate, sulfate or lactate, ($C_8$-$C_{22}$)-alkylamidopropyltrimethylammonium chloride or methosulfate, N,N-bis (2-$C_8$-$C_{22}$-alkanoyloxyethyl)dimethylammonium chloride or methosulfate, N,N-bis(2-$C_8$-$C_{22}$-alkanoyloxyethyl)hydroxyethylmethyl-ammonium chloride or methosuifate, and ester quats based on $C_8$-$C_{22}$ alkanoyl esters of triethanolamine or methyldiethanolamine.

The amount of the cationic surfactants in the inventive compositions is preferably from 0.1 to 10.0% by weight, more preferably from 0.5 to 7.0% by weight and especially preferably from 1.0 to 5.0% by weight, based on the total weight of the compositions.

Preferred nonionic surfactants are fatty alcohol ethoxylates (alkylpolyethylene glycols); alkylphenol polyethylene glycols; fatty amine ethoxylates (alkylaminopolyethylene glycols); fatty acid ethoxylates (acyl polyethylene glycols); polypropylene glycol ethoxylates (Pluronics®); fatty acid alkanolamides, (fatty acid amide polyethylene glycols); sucrose esters; sorbitol esters and sorbitan esters and polyglycol ethers thereof, and also $C_8$-$C_{22}$-alkyl polyglucosides.

The amount of the nonionic surfactants in the inventive compositions (for example in the case of rinse-off products) is preferably in the range from 0.05 to 20.0% by weight, more preferably from 0.1 to 10.0% by weight and especially preferably from 0.5 to 5.0% by weight, based on the total weight of the compositions.

In addition, the inventive compositions may comprise amphoteric surfactants. These can be described as derivatives of long-chain secondary or tertiary amines which have an alkyl group with 8 to 18 carbon atoms and in which a further group is substituted by an anionic group which imparts the solubility in water, thus, for example, by a carboxyl, sulfate or sulfonate group. Preferred amphoteric surfactants are N—($C_{12}$-$C_{18}$)-alkyl-β-amino-propionates and N—($C_{12}$-$C_{18}$)-alkyl-β-iminodipropionates as alkali metal and mono-, di- and trialkylammonium salts; suitable further surfactants are also amine oxides. These are oxides of tertiary amines with a long-chain group having 8 to 18 carbon atoms and two mostly short-chain alkyl groups having 1 to 4 carbon atoms. Preference is given here, for example, to the $C_{10}$- to $C_{18}$-alkyldimethylamine oxides, fatty acid amidoalkyldimethylamine oxide.

A further preferred group of surfactants is betaine surfactants, also known as zwitterionic surfactants. These contain, in the same molecule, a cationic group, especially an ammonium group, and an anionic group, which may be a carboxylate group, sulfate group or sulfonate group. Suitable betaines are preferably alkylbetaines such as cocobetaine or fatty acid alkyl-amidopropyl betaines, for example cocoacylamidopropyl dimethyl betaine or the $C_{12}$- to $C_{18}$-dimethylaminohexanoates and/or the $C_{10}$- to $C_{18}$-acyl-amidopropane dimethyl betaines.

The amount of the amphoteric surfactants and/or betaine surfactants in the inventive compositions is preferably from 0.5 to 20.0% by weight and more preferably from 1.0 to 10.0% by weight, based on the total weight of the compositions.

Preferred surfactants are lauryl sulfate, laureth sulfate, cocoamidopropyl betaine, alkyl betaines such as cocobetaine, sodium cocoylglutamate and lauroamphoacetate.

The inventive compositions may comprise, as further assistants and additives, oil bodies, silicone oils, waxes, emulsifiers, coemulsifiers, solubilizers, cationic polymers, film formers, superfatting agents, refatting agents, active antimicrobial ingredients, humectants, solvents, dyes, fragrances, pearlizing agents and/or opacifiers.

The oil bodies may advantageously be selected from the groups of triglycerides, natural and synthetic fatty substances, preferably esters of fatty acids with alcohols of low carbon number, for example with isopropanol, propylene glycol or glycerol, or esters of fatty alcohols with alkanoic acids of low carbon number or with fatty acids or from the group of alkyl benzoates, and also natural or synthetic hydrocarbon oils.

Useful substances include triglycerides of linear or branched, saturated or unsaturated, optionally hydroxylated, $C_8$-$C_{30}$-fatty acids, in particular vegetable oils, such as sunflower oil, corn oil, soybean oil, rice oil, jojoba oil, babassu oil, pumpkin oil, grapeseed oil, sesame oil, walnut oil, apricot oil, orange oil, wheatgerm oil, peach kernel oil, macadamia oil, avocado oil, sweet almond oil, lady's smock oil, castor oil, olive oil, peanut oil, rapeseed oil and coconut oil, and also synthetic triglyceride oils, e.g. the commercial product Myritol® 318. Hydrogenated triglycerides are also preferred in accordance with the invention. Oils of animal origin, for example beef tallow, perhydrosqualene, lanolin, can also be used.

A further class of preferred oil bodies is that of the benzoic esters of linear or branched $C_{8-22}$-alkanols, e.g. the commercial products Finsoly® SB (isostearyl benzoate), Finsolv® TN($C_{12}$-$C_{15}$-alkyl benzoate) and Finsolv® EB (ethylhexyl benzoate).

A further class of preferred oil bodies is that of the dialkyl ethers having a total of 12 to 36 carbon atoms, especially having 12 to 24 carbon atoms, for example di-n-octyl ether (Cetiol® OE), di-n-nonyl ether, di-n-decyl ether, di-n-undecyl ether, di-n-dodecyl ether, n-hexyl n-octyl ether, n-octyl n-decyl ether, n-decyl n-undecyl ether, n-undecyl n-dodecyl ether and n-hexyl n-undecyl ether, di-3-ethyldecyl ether, tert-butyl n-octyl ether, isopentyl n-octyl ether and 2-methylpentyl n-octyl ether, and di-tert-butyl ether and diisopentyl ether.

Likewise useful are branched saturated or unsaturated fatty alcohols having 6-30 carbon atoms, e.g. isostearyl alcohol, and Guerbet alcohols.

A further class of preferred oil bodies is that of alkyl hydroxycarboxylates. Preferred alkyl hydroxycarboxylates are full esters of glycolic acid, lactic acid, malic acid, tartaric acid or citric acid. Further esters of hydroxy-carboxylic acids which are suitable in principle are esters of β-hydroxypropionic acid, of tartronic acid, of D-gluconic acid, sugar acid, mucic acid or glucuronic acid. Suitable alcohol components of these esters are primary, linear or branched aliphatic alcohols having 8 to 22 carbon atoms. The esters of $C_{12}$-$C_{15}$-fatty alcohols are particularly preferred. Esters of this type are commercially available, e.g. under the trade name Cosmacol® from EniChem, Augusta Industriale.

A further class of preferred oil bodies is that of dicarboxylic esters of linear or branched $C_2$-$C_{10}$-alkanols, such as di-n-butyl adipate (Cetiol® B), di(2-ethylhexyl) adipate and di(2-ethylhexyl) succinate, and also diol esters, such as ethylene glycol dioleate, ethylene glycol diisotridecanoate, propylene glycol di(2-ethylhexanoate), propylene glycol diisostearate, propylene glycol dipelargonate, butanediol diisostearate and neopentyl glycol dicaprylate, and also diisotridecyl azelate.

Likewise preferred oil bodies are symmetrical, asymmetrical or cyclic esters of carbonic acid with fatty alcohols, glycerol carbonate or dicaprylyl carbonate (Cetiol® CC).

A further class of preferred oil bodies is that of the esters of dimers of unsaturated $C_{12}$-$C_{22}$-fatty acids (dimer fatty acids) with monovalent linear, branched or cyclic $C_2$-$C_{18}$-alkanols or with polyvalent linear or branched $C_2$-$C_6$-alkanols.

A further class of preferred oil bodies is that of hydrocarbon oils, for example those with linear or branched, saturated or unsaturated $C_7$-$C_{40}$-carbon chains, for example Vaseline, dodecane, isododecane, cholesterol, lanolin, synthetic hydrocarbons such as polyolefins, in particular polyisobutene, hydrogenated polyisobutene, polydecane, and hexadecane, isohexadecane, paraffin oils, isoparaffin oils, e.g. the commercial products of the Permethyl® series, squalane, squalene, and alicyclic hydrocarbons, e.g. the commercial product 1,3-di(2-ethylhexyl)-cyclohexane (Cetiol® S), ozokerite, and ceresine.

Available silicone oils and silicone waxes are preferably dimethylpolysiloxanes and cyclomethicones, polydialkylsiloxanes $R_3SiO(R_2SiO)_xSiR_3$ where R is methyl or ethyl, more preferably methyl, and x is a number from 2 to 500, for example the dimethicones available under the trade names VICASIL (General Electric Company), DOW CORNING 200, DOW CORNING 225, DOW CORNING 200 (Dow Corning Corporation), and also the dimethicones available under SilCare® Silicone 41M65, SilCare® Silicone 41M70, SilCare® Silicone 41M80 (Clariant), stearyldimethylpolysiloxane, $C_{20}$-$C_{24}$-alkyldimethylpolysiloxane, $C_{24}$-$C_{28}$-alkyldimethylpolysiloxane, but also the methicones available as SilCare® Silicone 41M40, SilCare® Silicone 41M50 (Clariant), and also trimethyl-siloxysilicates $[(CH_2)_3SiO)_{1/2}]_x[SiO_2]_y$, where x is a number from 1 to 500 and y is a number from 1 to 500, dimethiconols $R_3SiO[R_2SiO]_xSiR_2OH$ and $HOR_2SiO[R_2SiO]_xSiR_2OH$, where R is methyl or ethyl and x is a number up to 500, polyalkylarylsiloxanes, for example the polymethylphenylsiloxanes available under the trade names SF 1075 METHYLPHENYL FLUID (General Electric Company) and 556 COSMETIC GRADE PHENYL TRIMETHICONE FLUID (Dow Corning Corporation), polydiarylsiloxanes, silicone resins, cyclic silicones and amino-, fatty acid-, alcohol-, polyether-, epoxy-, fluorine- and/or alkyl-modified silicone compounds, and also polyether siloxane copolymers.

The inventive compositions may comprise waxes, for example paraffin waxes, microwaxes and ozokerites, beeswax and its component fractions, and also beeswax derivatives, waxes from the group of homopolymeric polyethylenes or copolymers of α-olefins, and natural waxes such as rice wax, candelilla wax, carnauba wax, japan wax or shellac wax.

Emulsifiers, coemulsifiers and solubilizers which may be used are nonionic, anionic, cationic or amphoteric surface-active compounds.

Useful nonionogenic surface-active compounds are preferably:
addition products of from 0 to 30 mol of ethylene oxide and/or 0 to 5 mol of propylene oxide onto linear fatty alcohols having 8 to 22 carbon atoms, onto fatty acids having 12 to 22 carbon atoms, onto alkylphenols having 8 to 15 carbon atoms in the alkyl group and onto sorbitan or sorbitol esters; ($C_{12}$-$C_{18}$) fatty acid mono- and diesters of addition products of from 0 to 30 mol of ethylene oxide onto glycerol; glycerol mono- and diesters and sorbitan mono- and diesters of saturated and unsaturated fatty acids having 6 to 22 carbon atoms and optionally ethylene oxide addition products thereof; addition products of from 15 to 60 mol of ethylene oxide onto castor oil and/or hydrogenated castor oil; polyol and in particular polyglycerol esters, such as, for example, polyglycerol polyricinoleate and polyglycerol poly-12-hydroxystearate. Ethoxylated fatty amines, fatty acid amides, fatty acid alkanolamides and mixtures of compounds of two or more of these substance classes are likewise preferably suitable.

Suitable ionogenic coemulsifiers are, for example, anionic emulsifiers, such as mono-, di- or triphosphoric acid esters, soaps (e.g. sodium stearate), fatty alcohol sulfates, but also cationic emulsifiers such as mono-, di- and trialkyl quats and polymeric derivatives thereof.

Available amphoteric emulsifiers are preferably alkylaminoalkylcarboxylic acids, betaines, sulfo betaines and imidazoline derivatives.

Particular preference is given to using fatty alcohol ethoxylates selected from the group of ethoxylated stearyl alcohols, isostearyl alcohols, cetyl alcohols, isocetyl alcohols, oleyl alcohols, lauryl alcohols, isolauryl alcohols and cetylstearyl alcohols, in particular polyethylene glycol(13) stearyl ether, polyethylene glycol(14) stearyl ether, polyethylene glycol(15) stearyl ether, polyethylene glycol(16) stearyl ether, polyethylene glycol(17) stearyl ether, polyethylene glycol(18) stearyl ether, polyethylene glycol(19) stearyl ether, polyethylene glycol(20) stearyl ether, polyethylene glycol(12) isostearyl ether, polyethylene glycol(13) isostearyl ether, polyethylene glycol(14) isostearyl ether, polyethylene glycol(15) isostearyl ether, polyethylene glycol(16) isostearyl ether, polyethylene glycol(17) isostearyl ether, polyethylene glycol(18) isostearyl ether, polyethylene glycol(19) isostearyl ether, polyethylene glycol(20) isostearyl ether, polyethylene glycol(13) cetyl ether, polyethylene glycol(14) cetyl ether, polyethylene glycol(15) cetyl ether, polyethylene glycol(16) cetyl ether, polyethylene glycol(17) cetyl ether, polyethylene glycol(18) cetyl ether, polyethylene glycol(19) cetyl ether, polyethylene glycol(20) cetyl ether, polyethylene glycol(13) isocetyl ether, polyethylene glycol (14) isocetyl ether, polyethylene glycol(15) isocetyl ether, polyethylene glycol(16) isocetyl ether, polyethylene glycol (17) isocetyl ether, polyethylene glycol(18) isocetyl ether, polyethylene glycol(19) isocetyl ether, polyethylene glycol (20) isocetyl ether, polyethylene glycol(12) oleyl ether, polyethylene glycol(13) oleyl ether, polyethylene glycol(14) oleyl ether, polyethylene glycol(15) oleyl ether, polyethylene glycol(12) lauryl ether, polyethylene glycol(12) isolauryl ether, polyethylene glycol(13) cetylstearyl ether, polyethylene glycol(14) cetylstearyl ether, polyethylene glycol (15) cetylstearyl ether, polyethylene glycol(16) cetylstearyl ether, polyethylene glycol(17) cetylstearyl ether, polyethylene glycol(18) cetylstearyl ether, polyethylene glycol(19) cetylstearyl ether.

Likewise preferred are fatty acid ethoxylates selected from the group of ethoxylated stearates, isostearates and oleates, in particular polyethylene glycol(20) stearate, polyethylene glycol(21) stearate, polyethylene glycol(22) stearate, polyethylene glycol(23) stearate, polyethylene glycol (24) stearate, polyethylene glycol(25) stearate, polyethylene glycol(12) isostearate, polyethylene glycol(13) isostearate, polyethylene glycol(14) isostearate, polyethylene glycol(15) isostearate, polyethylene glycol(16) isostearate, polyethylene glycol(17) isostearate, polyethylene glycol(18) isostearate, polyethylene glycol(19) isostearate, polyethylene glycol(20) isostearate, polyethylene glycol(21) isostearate, polyethylene glycol(22) isostearate, polyethylene glycol(23) isostearate, polyethylene glycol(24) isostearate, polyethylene glycol(25) isostearate, polyethylene glycol(12) oleate, polyethylene glycol(13) oleate, polyethylene glycol(14) oleate, polyethylene glycol(15) oleate, polyethylene glycol (16) oleate, polyethylene glycol(17) oleate, polyethylene glycol(18) oleate, polyethylene glycol(19) oleate, polyethylene glycol(20)oleate.

Sodium laureth-11 carboxylate can advantageously be used as ethoxylated alkyl ether carboxylic acid or salts thereof.

It is additionally advantageous to select the polyethylene glycol glycerol fatty acid esters from the group polyethylene glycol(20) glyceryl laurate, polyethylene glycol(6) glyceryl caprate/caprinate, polyethylene glycol(20) glyceryl oleate, polyethylene glycol(20) glyceryl isostearate and polyethylene glycol(18) glyceryl oleate/cocoate.

Particularly suitable among the sorbitan esters are polyethylene glycol(20) sorbitan monolaurate, polyethylene glycol(20) sorbitan monostearate, polyethylene glycol(20) sorbitan monoisostearate, polyethylene glycol(20) sorbitan monopaimitate, polyethylene glycol(20) sorbitan monooleate.

Particularly advantageous coemulsifiers are giyceryl monostearate, glyceryl monooleate, diglyceryl monostearate, glyceryl isostearate, polyglyceryl-3 oleate, polyglyceryl-3 diisostearate, polyglyceryl-4 isostearate, polyglyceryl-2 dipolyhydroxystearate, polyglyceryl-4 dipolyhydroxystearate, PEG-30 dipolyhydroxystearate, diisostearoyl polyglyceryl-3 diisostearate, glycol distearate and polyglyceryl-3 dipolyhydroxystearate, sorbitan monoisostearate, sorbitan stearate, sorbitan oleate, sucrose distearate, lecithin, PEG-7-hydrogenated castor oil, cetyl alcohol, stearyl alcohol, behenyl alcohol, isobehenyl alcohol and polyethylene glycol(2) stearyl ether (steareth-2), alkylmethicone copolyols and alkyldimethicone copolyols, in particular cetyldimethicone copolyol, laurylmethicone copolyol.

The inventive compositions may comprise one or more of the emulsifiers, coemulsifiers or solubilizers in amounts of 0.1 to 20.0% by weight, preferably of 1.0 to 15.0% by weight and more preferably of 3.0% to 10.0% by weight, based on the total weight of the compositions.

Suitable cationic polymers are those known under the INCl name "Polyquaternium", in particular Polyquaternium-31, Polyquaternium-16, Polyquaternium-24, Polyquaternium-7, Polyquaternium-22, Polyquaternium-39, Polyquaternium-28, Polyquaternium-2, Polyquaternium-10, Polyquaternium-11, and Polyquaternium 37&mineral oil&PPG trideceth (Salcare SC95), PVP-dimethylaminoethyl methacrylate copolymer, guar hydroxypropyltriammonium chloride, and calcium alginate and ammonium alginate. Furthermore, cationic cellulose derivatives; cationic starch; copolymers of diallylammonium salts and acrylamides; quaternized vinylpyrrolidone/vinylimidazole polymers; condensation products of polyglycols and amines; quaternized collagen polypeptides; quaternized wheat polypeptides; polyethyleneimines; cationic silicone polymers, such as, for example, amidomethicones; copolymers of adipic acid and dimethylaminohydroxypropyldiethylenetriamine; polyamino-polyamide and cationic chitin derivatives, such as, for example, chitosan, can be used.

The inventive compositions can comprise one or more of the aforementioned cationic polymers in amounts of 0.1% to 5.0% by weight, preferably 0.2% to 3.0% by weight and particularly preferably 0.5% to 2.0% by weight, based on the total weight of the compositions.

In addition, the inventive compositions may comprise film formers which, depending on the intended use, are selected, for example, from salts of phenylbenzimidazolesulfonic acid, water-soluble polyurethanes, for example $C_{10}$-polycarbamyl polyglyceryl ester, polyvinyl alcohol, polyvinylpyrrolidone copolymers, for example vinylpyrrolidone/vinyl acetate copolymer, water-soluble acrylic acid polymers/copolymers and esters or salts thereof.

The inventive compositions may comprise one or more film formers in amounts of 0.1% to 10.0% by weight, preferably 0.2% to 5% by weight and more preferably 0.5% to 3.0% by weight, based on the total weight of the compositions.

Superfatting agents which may be used are, preferably lanolin and lecithin, nonethoxylated and polyethoxylated or acylated lanolin derivatives and lecithin derivatives, polyol fatty acid esters, mono-, di- and triglycerides and/or fatty acid alkanolamides, where the latter simultaneously serve as foam stabilizers, which are preferably used in amounts of 0.01% to 10.0% by weight, more preferably of 0.1% to 5.0% by weight and especially preferably of 0.5% to 3.0% by weight, based on the total weight of the compositions.

Antimicrobial active ingredients which may be used are cetyltrimethylammonium chloride, cetylpyridinium chloride, benzethonium chloride, diisobutylethoxyethyldimethylbenzylammonium chloride, sodium aluminum chlorohydroxylactate, triethyl citrate, 2,4,4'-trichloro-2'-hydroxydiphenyl ether (triclosan), 3,4,4'-trichlorocarbanilide (triclocarban), diaminoalkyl-amide, for example L-lysine hexadecylamide, citrate heavy metal salts, salicylates, pyrithiones and heavy metal salts thereof, especially zinc pyrithione, farnesol, ketoconazole, oxiconazole, bifonazole, butoconazole, cloconazole, clotrimazole, econazole, enilconazole, fenticonazole, isoconazole, miconazole, sulconazole, tioconazole, fluconazole, itraconazole, terconazole, naftifine and terbinafine, selenium disulfide, iodopropynyl butylcarbamate, methylchloroisothiazolinone, methyl-isothiazolinone, methyldibromoglutaronitrile, AgCl, chloroxylenol, sodium benzoate, and phenoxyethanoi, phenoxyisopropanol, parabens, preferably butyl, ethyl, methyl and propyl paraben, and sodium salts thereof, pentanediol, 1,2-hexanediol, 1,2-octanediol, 2-bromo-2-nitropropane-1,3-diol, ethylhexylglycerol, benzyl alcohol, sorbic acid, benzoic acid, lactic acid, imidazolidinylurea, diazolidinylurea, dimethyloldimethylhydantoin (DMDMH), sodium salt of hydroxymethylglycinate.

The inventive compositions comprise the active antimicrobial ingredients preferably in amounts from 0.001% to 5.0% by weight, more preferably from 0.01% to 3.0% by weight, and with particular preference from 0.1% to 2.0% by weight, based on the total weight of the compositions.

In addition, it is possible to use humectants selected from the sodium salt of 2-pyrrolidone-5-carboxylate (NaPCA), guanidine; glycolic acid and salts thereof, lactic acid and salts thereof, glucosamines and salts thereof, lactamide monoethanolamine, acetamide monoethanolamine, urea, hydroxy acids, panthenol and derivatives thereof, for example D-panthenol (R-2,4-dihydroxy-N-(3-hydroxypropyl)-3,3-dimethylbutamide), DL-panthenol, calcium pantothenate, panthetine, pantotheine, panthenyl ethyl ether, isopropyl palmitate, glycerol and/or sorbitol, preferably in amounts of from 0.1% to 15.0% by weight and particularly preferably from 0.5% to 5.0% by weight, based on the total weight of the compositions.

Additionally, the inventive compositions may comprise organic solvents. In principle, suitable organic solvents are all mono- or polyhydric alcohols. Preference is given to using alcohols having 1 to 4 carbon atoms, such as ethanol, propanol, isopropanol, n-butanol, isobutanol, tert-butanol, glycerol and mixtures of said alcohols. Further preferred alcohols are polyethylene glycols with a relative molecular mass below 2000. In particular, the use of polyethylene glycol with a relative molecular mass between 200 and 600 and in amounts up to 45.0% by weight and of polyethylene glycol with a relative molecular mass between 400 and 600 in amounts of from 5.0% to 25.0% by weight is preferred. Further suitable solvents are, for example, triacetin (glycerol triacetate) and 1-methoxy-2-propanol.

The inventive compositions may comprise dyes and/or pigments, either organic or inorganic dyes selected from the corresponding positive list of the German Cosmetics Act or from the EC list of cosmetic colorants.

| Chemical or other name | CIN | Color |
|---|---|---|
| Pigment Green | 10006 | green |
| Acid Green 1 | 10020 | green |
| 2,4-Dinitrohydroxynaphthalene-7-sulfonic acid | 10316 | yellow |
| Pigment Yellow 1 | 11680 | yellow |
| Pigment Yellow 3 | 11710 | yellow |
| Pigment Orange 1 | 11725 | orange |
| 2,4-Dihydroxyazobenzene | 11920 | orange |
| Solvent Red 3 | 12010 | red |
| 1-(2'-Chloro-4'-nitro-1'-phenylazo)-2-hydroxynaphthalene | 12085 | red |
| Pigment Red 3 | 12120 | red |
| Cerise Red; Sudan Red; Fat Red G | 12150 | red |
| Pigment Red 112 | 12370 | red |
| Pigment Red 7 | 12420 | red |
| Pigment Brown 1 | 12480 | brown |
| 4-(2'-Methoxy-5'-sulfonic acid diethylamide-1'-phenylazo)-3-hydroxy-5"-chloro-2",4"-dimethoxy-2-naphthanilide | 12490 | red |
| Disperse Yellow 16 | 12700 | yellow |
| 1-(4-Sulfo-1-phenylazo)-4-aminobenzenesulfonic acid | 13015 | yellow |
| 2,4-Dihydroxyazobenzene-4'-sulfonic acid | 14270 | orange |
| 2-(2,4-Dimethylphenylazo-5-sulfonic acid)-1-hydroxynaphthalene-4-sulfonic acid | 14700 | red |
| 2-(4-Sulfo-1-naphthylazo)-1-naphthol-4-sulfonic acid | 14720 | red |
| 2-(6-Sulfo-2,4-xylylazo)-1-naphthol-5-sulfonic acid | 14815 | red |
| 1-(4'-Sulfophenylazo)-2-hydroxynaphthalene | 15510 | orange |
| 1-(2-Sulfonic acid-4-chloro-5-carboxylic acid-1-phenylazo)-2-hydroxynaphthalene | 15525 | red |
| 1-(3-Methylphenylazo-4-sulfonic acid)-2-hydroxynaphthalene | 15580 | red |
| 1-(4',(8')-Sulfonic acid naphthylazo)-2-hydroxynaphthalene | 15620 | red |
| 2-Hydroxy-1,2'-azonaphthalene-1'-sulfonic acid | 15630 | red |
| 3-Hydroxy-4-phenylazo-2-naphthylcarboxylic acid | 15800 | red |
| 1-(2-Sulfo-4-methyl-1-phenylazo)-2-naphthylcarboxylic acid | 15850 | red |
| 1-(2-Sulfo-4-methyl-5-chloro-1-phenylazo)-2-hydroxynaphthalene-3-carboxylic acid | 15865 | red |
| 1-(2-Sulfo-1-naphthylazo)-2-hydroxynaphthalene-3-carboxylic acid | 15880 | red |
| 1-(3-Sulfo-1-phenylazo)-2-naphthol-6-sulfonic acid | 15980 | orange |
| 1-(4-Sulfo-1-phenylazo)-2-naphthol-6-sulfonic acid | 15985 | yellow |
| Allura Red | 16035 | red |
| 1-(4-Sulfo-1-naphthylazo)-2-naphthol-3,6-disulfonic acid | 16185 | red |
| Acid Orange 10 | 16230 | orange |
| 1-(4-Sulfo-1-naphthylazo)-2-naphthol-6,8-disulfonic acid | 16255 | red |
| 1-(4-Sulfo-1-naphthylazo)-2-naphthol-3,6,8-trisulfonic acid | 16290 | red |
| 8-Amino-2-phenylazo-1-naphthol-3,6-disulfonic acid | 17200 | red |
| Acid Red 1 | 18050 | red |
| Acid Red 155 | 18130 | red |
| Acid Yellow 121 | 18690 | yellow |
| Acid Red 180 | 18736 | red |
| Acid Yellow 11 | 18820 | yellow |
| Acid Yellow 17 | 18965 | yellow |
| 4-(4-Sulfo-1-phenylazo)-1-(4-sulfophenyl)-5-hydroxypyrazolone-3-carboxylic acid | 19140 | yellow |
| Pigment Yellow 16 | 20040 | yellow |
| 2,6-(4'-Sulfo-2",4"-dimethyl)bisphenylazo)-1,3-dihydroxybenzene | 20170 | orange |
| Acid Black 1 | 20470 | black |
| Pigment Yellow 13 | 21100 | yellow |
| Pigment Yellow 83 | 21108 | yellow |
| Solvent Yellow | 21230 | yellow |
| Acid Red 163 | 24790 | red |
| Acid Red 73 | 27290 | red |
| 2-[4'-(4"-Sulfo-1"-phenylazo)-7'-sulfo-1'-naphthylazo]-1-hydroxy-7-aminonaphthalene-3,6-disulfonic acid | 27755 | black |
| 4'-[(4"-Sulfo-1"-phenylazo)-7'-sulfo-1'-naphthylazo]-1-hydroxy-8-acetylaminonaphthalene-3,5-disulfonic acid | 28440 | black |
| Direct Orange 34, 39, 44, 46, 60 | 40215 | orange |
| Food Yellow | 40800 | orange |
| trans-β-Apo-8'-Carotenealdehyde ($C_{30}$) | 40820 | orange |
| trans-Apo-8'-Carotenoic acid ($C_{30}$)-ethyl ester | 40825 | orange |
| Canthaxanthin | 40850 | orange |
| Acid Blue 1 | 42045 | blue |
| 2,4-Disulfo-5-hydroxy-4'-4"-bis(diethylamino)triphenyl-carbinol | 42051 | blue |
| 4-[(4-N-Ethyl-p-sulfobenzylamino)phenyl-(4-hydroxy-2-sulfophenyl)(methylene)-1-(N-ethyl-N-p-sulfobenzyl)-2,5-cyclohexadieneimine] | 42053 | green |
| Acid Blue 7 | 42080 | blue |
| (N-Ethyl-p-sulfobenzylaminophenyl-(2-sulfophenyl)-methylene-(N-ethyl-N-p-sulfobenzyl)cyclohexadieneimine | 42090 | blue |
| Acid Green 9 | 42100 | green |
| Diethyldisulfobenzyldi-4-amino-2-chlorodi-2-methyl-fuchsonimmonium | 42170 | green |
| Basic Violet 14 | 42510 | violet |
| Basic Violet 2 | 42520 | violet |

-continued

| Chemical or other name | CIN | Color |
|---|---|---|
| 2'-Methyl-4'-(N-ethyl-N-m-sulfobenzyl)amino-4''-(N-diethyl)-amino-2-methyl-N-ethyl-N-m-sulfobenzyl-fuchsonimmonium | 42735 | blue |
| 4'-(N-Dimethyl)amino-4''-(N-phenyl)aminonaphtho-N-dimethylfuchsonimmonium | 44045 | blue |
| 2-Hydroxy-3,6-disulfo-4,4'-bisdimethylaminonaphtho-fuchsinimmonium | 44090 | green |
| Acid red | 45100 | red |
| 3-(2'-Methylphenylamino)-6-(2'-methyl-4'-sulfophenyl-amino)-9-(2''-carboxyphenyl)xanthenium salt | 45190 | violet |
| Acid Red 50 | 45220 | red |
| Phenyl-2-oxyfluorone-2-carboxylic acid | 45350 | yellow |
| 4,5-Dibromofluorescein | 45370 | orange |
| 2,4,5,7-Tetrabromofluorescein | 45380 | red |
| Solvent Dye | 45396 | orange |
| Acid Red 98 | 45405 | red |
| 3',4',5',6'-Tetrachloro-2,4,5,7-tetrabromofluorescein | 45410 | red |
| 4,5-Diiodofluorescein | 45425 | red |
| 2,4,5,7-Tetraiodofluorescein | 45430 | red |
| Quinophthalone | 47000 | yellow |
| Quinophthalonedisulfonic acid | 47005 | yellow |
| Acid Violet 50 | 50325 | violet |
| Acid Black 2 | 50420 | black |
| Pigment Violet 23 | 51319 | violet |
| 1,2-Dioxyanthraquinone, calcium-aluminum complex | 58000 | red |
| 3-Oxypyrene-5,8,10-sulfonic acid | 59040 | green |
| 1-Hydroxy-4-N-phenylaminoanthraquinone | 60724 | violet |
| 1-Hydroxy-4-(4'-methylphenylamino)anthraquinone | 60725 | violet |
| Acid Violet 23 | 60730 | violet |
| 1,4-Di(4'-methylphenylamino)anthraquinone | 61565 | green |
| 1,4-Bis(o-sulfo-p-toluidine)anthraquinone | 61570 | green |
| Acid Blue 80 | 61585 | blue |
| Acid Blue 62 | 62045 | blue |
| N,N'-Dihydro-1,2,1',2'-anthraquinoneazine | 69800 | blue |
| Vat Blue 6; Pigment Blue 64 | 69825 | blue |
| Vat Orange 7 | 71105 | orange |
| Indigo | 73000 | blue |
| Indigodisulfonic acid | 73015 | blue |
| 4,4'-Dimethyl-6,6'-dichlorothioindigo | 73360 | red |
| 5,5'-Dichloro-7,7'-dimethylthioindigo | 73385 | violet |
| Quinacridone Violet 19 | 73900 | violet |
| Pigment Red 122 | 73915 | red |
| Pigment Blue 16 | 74100 | blue |
| Phthalocyanine | 74160 | blue |
| Direct Blue 86 | 74180 | blue |
| Chlorinated phthalocyanines | 74260 | green |
| Natural Yellow 6,19; Natural Red 1 | 75100 | yellow |
| Bixin, Nor-Bixin | 75120 | orange |
| Lycopene | 75125 | yellow |
| trans-alpha, beta- or gamma-Carotene | 75130 | orange |
| Keto and/or hydroxyl derivatives of carotene | 75135 | yellow |
| Guanine or pearlescent agents | 75170 | white |
| 1,7-Bis(4-hydroxy-3-methoxyphenyl)-1,6-heptadiene-3,5-dione | 75300 | yellow |
| Complex salt (Na,Al,Ca) of carminic acid | 75470 | red |
| Chlorophyll a and b; copper compounds of the chlorophylls and chlorophyllines | 75810 | green |
| Aluminum | 77000 | white |
| Aluminum hydrate | 77002 | white |
| Water-containing aluminum silicates | 77004 | white |
| Ultramarine | 77007 | blue |
| Pigment Red 101 and 102 | 77015 | red |
| Barium sulfate | 77120 | white |
| Bismuth oxychloride and its mixtures with mica | 77163 | white |
| Calcium carbonate | 77220 | white |
| Calcium sulfate | 77231 | white |
| Carbon | 77266 | black |
| Pigment Black 9 | 77267 | black |
| Carbo medicinalis vegetabilis | 77268:1 | black |
| Chromic oxide | 77288 | green |
| Chromium oxide, hydrated | 77289 | green |
| Pigment Blue 28, Pigment Green 14 | 77346 | green |
| Pigment Metal 2 | 77400 | brown |
| Gold | 77480 | brown |
| Iron oxides and hydroxides | 77489 | orange |
| Iron oxides and hydroxides | 77491 | red |
| Hydrated iron oxide | 77492 | yellow |
| Iron oxide | 77499 | black |
| Mixtures of iron(II) and iron(III) hexacyanoferrate | 77510 | blue |
| Pigment White 18 | 77713 | white |
| Manganese ammonium diphosphate | 77742 | violet |
| Manganese phosphate; $Mn_3(PO_4)_2 \cdot 7H_2O$ | 77745 | red |
| Silver | 77820 | white |
| Titanium dioxide and its mixtures with mica | 77891 | white |
| Zinc oxide | 77947 | white |
| 6,7-Dimethyl-9-(1'-D-ribityl)isoalloxazine, lactoflavin | | yellow |
| Caramel | | brown |
| Capsanthin, Capsorubin | | orange |
| Betanine | | red |
| Benzopyrilium salts, anthocyanines | | red |
| Aluminum, zinc, magnesium and calcium stearate | | white |
| Bromothymol Blue | | blue |
| Bromocresol Green | | green |
| Acid Red 195 | | red |

Also advantageous are oil-soluble natural dyes, for example paprika extracts, β-carotene and cochineal.

Fragrance and/or perfume oils which may be used are individual odorant compounds, e.g. the synthetic products of the ester, ether, aldehyde, ketone, alcohol and hydrocarbon types. Odorant compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allyl cyclohexyl propionate, styrallyl propionate and benzyl salicylate. The ethers include, for example, benzyl ethyl ethers, the aldehydes include, for example, the linear alkanals having 8 to 18 carbon atoms, citral, citronellal, citronellyloxyacetaldehyde, cyclamenaldehyde, hydroxycitronellal, lilial and bourgeonal, the ketones include, for example, the ionones, alpha-isomethylionone and methyl cedryl ketone, the alcohols include anethol, citronellol, eugenol, geraniol, linalool, phenylethyl alcohol and terpineol, and the hydrocarbons include primarily the terpenes and balsams. Preference is given to using mixtures of different odorants which together produce a pleasing scent note.

Perfume oils may also comprise natural odorant mixtures, as are accessible from vegetable or animal sources, e.g. pine oil, citrus oil, jasmine oil, lily oil, rose oil or ylang-ylang oil. Essential oils of relatively low volatility which are usually used as aromatic components are also suitable as perfume oils, e.g. sage oil, chamomile oil, clove oil, melissa oil, mint oil, cinnamon leaf oil, linden blossom oil, juniperberry oil, vetiver oil, olibanum oil, galbanum oil and ladanum oil.

Preferentially suitable pearlizing components are fatty acid monoalkanol-amides, fatty acid dialkanolamides, monoesters or diesters of alkylene glycols, in particular ethylene glycol and/or propylene glycol or oligomers thereof, with higher fatty acids, such as, for example, palmitic acid, stearic acid and behenic acid, monoesters or polyesters of glycerol with carboxylic acids, fatty acids and metal salts thereof, ketosulfones or mixtures of the specified compounds. Particular preference is given to ethylene glycol distearates and/or polyethylene glycol distearates having an average of 3 glycol units.

Where the inventive compositions comprise pearlizing compounds, these are preferably present in the inventive compositions in an amount of 0.1 to 15.0% by weight and more preferably in an amount of 1.0 to 10.0% by weight, based on the total weight of the compositions.

As acids or alkalis for pH adjustment it is possible with preference to use mineral acids, more particularly HCl, inorganic bases, especially NaOH or KOH, and organic acids, especially citric acid.

The inventive compositions preferably have a pH of 2 to 10, more preferably from 2 to 7 and especially preferably from 2.5 to 4.5.

In a further preferred embodiment of the invention, the inventive compositions are compositions for bleaching and/or coloring of hair or a permanent wave formulation.

In a further preferred embodiment of the invention, the inventive compositions are oxidative cleaner formulations.

In a further preferred embodiment of the invention, the inventive compositions are stain removal gels for pretreatment of laundry, prewash sprays, stain removers, surface cleaners, toilet cleaners, multifunctional stain removal gels or bleaching gels.

In a further preferred embodiment of the invention, the inventive compositions are hair coloring compositions for prevention of bleaching damage in the course of hair coloring.

Hydroxypyridones and salts thereof are advantageously suitable for stabilization of one or more polymers having thickening properties. The present invention therefore further relates to use of one or more substances selected from the group consisting of hydroxypyridones and salts thereof for stabilization of one or more polymers having thickening properties, preferably in an inventive composition. The inventive compositions are preferably compositions for bleaching and/or coloring of hair, permanent wave formulations or oxidative cleaner formulations.

The one or more polymers having thickening properties to be stabilized are preferably selected from partly or fully neutralized polymers containing sulfo groups.

The one or more partly or fully neutralized polymers containing sulfo groups here are preferably selected from the group consisting of homo- or copolymers of acrylamidomethylpropanesulfonic acid and salts thereof.

The hydroxypyridones and salts thereof, which can be used as just described for stabilization in accordance with the invention, are the compounds of the formula (I) and salts thereof specified in the context of the description of the inventive compositions. Preference is given to stabilization using those compounds of the formula (I) and salts thereof which have also been listed as preferred in the description of the inventive compositions.

The examples and applications which follow are intended to illustrate the invention in detail, but without restricting it thereto. All percentages are % by weight (% by wt.), unless explicitly stated otherwise.

TEST EXAMPLES

Example 1

Hydrogen Peroxide Gel Thickened with an Associative Thickener

Formulation:

| | |
|---|---|
| Water, demineralized | ad 100% by wt. |
| Hydrogen peroxide solution (Solvay, 35% by wt., aqueous) | 17% by wt. |
| Triceteareth-50 Phosphate (Substance according to example 1 from DE 10 2008 006858) | 6% by wt. |
| 4-Methyl-6-(2,4,4-trimethylpentyl)-1-hydroxy-2-pyridone | 0.00077% by wt. |

The formulation was produced by dissolving the polymeric thickener in water, then mixing in the hydrogen peroxide solution and adjusting the formulation to the respective start pH with 10% by weight aqueous phosphoric acid. Each formulation was produced with and without addition of 7.7 ppm (0.00077% by wt.) of 4-methyl-6-(2,4,4-trimethylpentyl)-251-hydroxy-2-pyridone. For this purpose, 10 ml of a 0.1% by weight solution of the stabilizer in propylene glycol were dissolved in 1 liter of water and this solution was used as the water phase. A blank test with propylene glycol ruled out any influence of the solvent. The results of the viscosity measurements are shown in table 1.

TABLE 1

Results of viscosity measurements

| Start pH | 7.7 ppm of 4-methyl-6-(2,4,4-trimethyl-pentyl)-1-hydroxy-2-pyridone | Viscosity [mPa · s] immediate | Viscosity [mPa · s] after 4 weeks 40° C. | Viscosity [mPa · s] after 8 weeks 40° C. | Viscosity [mPa · s] after 12 weeks 40° C. |
|---|---|---|---|---|---|
| 3.9 | no | 12 000 | 8000 | 4070 | 690 |
| 3.3 | no | 10 400 | 1600 | 715 | 207 |
| 3.9 | yes | 13 400 | 9100 | 7850 | 5350 |
| 3.2 | yes | 11 200 | 8150 | 7300 | 5550 |

At the same time, the hydrogen peroxide content was determined iodometrically in each case. Over the entire storage time, this remained constant at 6.2-6.7% by weight.

The test result shows that the addition of the 4-methyl-6-(2,4,4-trimethylpentyl)-1-hydroxy-2-pyridone stabilizer, compared to an unstabilized sample, shows a distinctly reduced decline in viscosity, and hence significantly increases the stability of the thickener polymer.

Example 2

Hydrogen Peroxide Gel Thickened with a Sulfonate Copolymer

Formulation:

| | |
|---|---|
| Water, demineralized | ad 100% by wt. |
| Hydrogen peroxide solution (Solvay, 35% by wt., aqueous) | 17% by wt. |
| Aristoflex ® TAC (Ammonium Acryloyl Dimethyltaurate/Carboxyethyl Acrylate Crosspolymer) | 1.5% by wt. |
| 4-Methyl-6-(2,4,4-trimethylpentyl)-1-hydroxy-2-pyridone | 0.00088% by wt. |

The formulation was produced by dissolving the polymeric thickener in water and then mixing in the hydrogen peroxide solution. The respective start pH was subsequently established with 10% by weight aqueous phosphoric acid.

The formulation was produced in each case with and without addition of 8.8 ppm (0.00088% by wt.) of 4-methyl-6-(2,4,4-trimethylpentyl)-1-hydroxy-2-pyridone.

For this purpose, 10 ml of a 0.1% by weight solution of the stabilizer in propylene glycol were dissolved in 1 liter of water and this solution was used as the water phase. A blank test with propylene glycol ruled out any influence of the solvent. The results of the viscosity measurements are shown in table 2.

TABLE 2

Results of viscosity measurements

| Start pH | 8.8 ppm of 4-methyl-6-(2,4,4-trimethyl-pentyl)-1-hydroxy-2-pyridone | Viscosity [mPa · s] immediate | Viscosity [mPa · s] after 4 weeks 40° C. | Viscosity [mPa · s] after 8 weeks 40° C. | Viscosity [mPa · s] after 12 weeks 40° C. |
|---|---|---|---|---|---|
| 4.0 | no | 3000 | 408 | 10 | 10 |
| 3.2 | no | 2900 | 590 | 10 | 10 |
| 4.1 | yes | 3050 | 2100 | 2530 | 2280 |
| 3.49 | yes | 2870 | 2440 | 2300 | 2070 |

At the same time, the hydrogen peroxide content was determined iodometrically in each case. Over the entire storage time, this remained virtually constant at 5.8-6.3% by weight.

The test result shows that the addition of the 4-methyl-6-(2,4,4-trimethyl-pentyl)-1-hydroxy-2-pyridone stabilizer, compared to an unstabilized sample, shows a distinctly reduced decline in viscosity, and hence significantly increases the stability of the thickener polymer.

Example 3

Hydrogen Peroxide Gel Thickened with a Sulfonate Copolymer

Formulation:

| | |
|---|---|
| Water, demineralized | ad 100% by wt. |
| Hydrogen peroxide solution (Evonik, 50% by wt., aqueous) | 12.14% by wt. |
| Aristoflex ® AVS Sodium Acryloyldimethyltaurate/VP Crosspolymer | 0.5% by wt. |
| 4-Methyl-6-(2,4,4-trimethylpentyl)-1-hydroxy-2-pyridone | 0.00087% by wt. |

The formulation was produced by dissolving the polymeric thickener in water and then mixing in the hydrogen peroxide solution. The respective start pH was subsequently established with 10% by weight aqueous phosphoric acid. The formulation was produced in each case with and without addition of 8.7 ppm (0.00087% by wt.) of 4-methyl-6-(2,4,4-trimethylpentyl)-1-hydroxy-2-pyridone.

For this purpose, 10 ml of a 0.1% by weight solution of the stabilizer in propylene glycol were dissolved in 1 liter of water and this solution was used as the water phase. A blank test with propylene glycol ruled out any influence of the solvent. The results of the viscosity measurements are shown in table 3.

TABLE 3

Results of viscosity measurements

| Start pH | 8.7 ppm (=0.00087% by wt.) of 4-methyl-6-(2,4,4-trimethyl-pentyl)-1-hydroxy-2-pyridone | Viscosity [mPa · s] immediate | Viscosity [mPa · s] after 4 weeks 40° C. |
|---|---|---|---|
| 3.90 | no | 12 700 | 10 |
| 3.42 | no | 10 600 | 10 |
| 3.9 | yes | 15 700 | 16 000 |
| 3.29 | yes | 10 200 | 8800 |

At the same time, the hydrogen peroxide content was determined iodometrically in each case. Over the entire storage time, this remained virtually constant at 5.8-6.3% by weight.

The test result shows that the addition of the 4-methyl-6-(2,4,4-trimethyl-pentyl)-1-hydroxy-2-pyridone stabilizer, compared to an unstabilized sample, shows a distinctly reduced decline in viscosity, and hence significantly increases the stability of the thickener polymer.

Hydrogen peroxide was purchased from Solvay (35% by weight, aqueous, Interox® AG-CO-35) or Evonik (50% by weight, aqueous, B7 quality).

The viscosities were measured with a Brookfield model DV II viscometer, the spindles from the RV spindle set at 20 revolutions/minute and 20° C. Spindles 1 to 7 from the RV spindle set are used. Under these measurement conditions, spindle 1 is selected for viscosities not exceeding 500 mPa·s, spindle 2 for viscosities not exceeding 1000 mPa·s, spindle 3 for viscosities not exceeding 5000 mPa·s, spindle 4 for viscosities not exceeding 10 000 mPa·s, spindle 5 for viscosities not exceeding 20 000 mPa·s, spindle 6 for viscosities not exceeding 50 000 mPa·s and spindle 7 for viscosities not exceeding 200 000 mPa·s.

Example 4

Hydrogen Peroxide Gel Thickened with a Sulfonate Copolymer Formulation

| | |
|---|---|
| Water, demineralized | ad 100% by wt. |
| Hydrogen peroxide solution (Evonik, 50% by wt., aqueous) | 12.14% by wt. |
| Aristoflex ® AVS Sodium Acryloyldimethyltaurate/VP Crosspolymer | 0.5% by wt. |
| 1-Hydroxy-2-pyridone | 0.001% by wt. |

The formulation was produced by dissolving the polymeric thickener in water and then mixing in the hydrogen peroxide solution. The respective start pH was subsequently established with 10% by weight aqueous phosphoric acid. The formulation was produced in each case with and without addition of 10 ppm (0.001% by wt.) of 1-hydroxy-2-pyridone. For this purpose, 10 ml of a 0.1% by weight solution of the stabilizer in propylene glycol were dissolved in 1 liter of water and this solution was used as the water phase. A blank test with propylene glycol ruled out any influence of the solvent. The results of the viscosity measurements are shown in table 4.

TABLE 4

Results of viscosity measurements

| Start pH | 10 ppm (=0.001% by wt.) of 1-hydroxy-2-pyridone | Viscosity [mPa · s] immediate | Viscosity [mPa · s] after 4 weeks 40° C. |
| --- | --- | --- | --- |
| 4.0 | no | 5850 | 10 |
| 3.0 | no | 5200 | 10 |
| 4.0 | yes | 6700 | 6100 |
| 3.0 | yes | 5900 | 5500 |

At the same time, the hydrogen peroxide content was determined iodometrically in each case. Over the entire storage time, this remained virtually constant at 5:8-6.3% by weight.

The test result shows that the addition of the 1-hydroxy-2-pyridone stabilizer, compared to an unstabilized sample, shows a distinctly reduced decline in viscosity, and hence significantly increases the stability of the thickener polymer.

Example 5

Hydrogen Peroxide Gel Thickened with a Biopolymer Formulation

| | |
| --- | --- |
| Water, demineralized | ad 100% by wt. |
| Hydrogen peroxide solution (Solvay, 35% by wt., aqueous) | 17% by wt. |
| Xanthan gum | 1.5% by wt. |
| 4-Methyl-6-(2,4,4-trimethylpentyl)-1-hydroxy-2-pyridone | 0.00081% by wt. |

The formulation was produced by dissolving the polymeric thickener in water and then mixing in the hydrogen peroxide solution. The respective start pH was subsequently established with 10% by weight aqueous phosphoric acid. The formulation was produced in each case with and without addition of 8.1 ppm (0.00081% by wt.) of 4-methyl-6-(2,4,4-trimethylpentyl)-1-hydroxy-2-pyridone.

For this purpose, 10 ml of a 0.1% by weight solution of the stabilizer in propylene glycol were dissolved in 1 liter of water and this solution was used as the water phase. A blank test with propylene glycol ruled out any influence of the solvent. The results of the viscosity measurements are shown in table 5.

TABLE 5

Results of viscosity measurements

| Start pH | 8.1 ppm (=0.00081% by wt.) of 4-methyl-6-(2,4,4-trimethyl-pentyl)-1-hydroxy-2-pyridone | Viscosity [mPa · s] immediate | Viscosity [mPa · s] after 4 weeks 40° C. |
| --- | --- | --- | --- |
| 4.0 | no | 3500 | 10 |
| 3.0 | no | 5000 | 10 |
| 4.0 | yes | 4000 | 4150 |
| 3.0 | yes | 4800 | 4700 |

At the same time, the hydrogen peroxide content was determined iodometrically in each case. Over the entire storage time, this remained virtually constant at 5.8-6.3% by weight.

The test result shows that the addition of the 4-methyl-6-(2,4,4-trimethyl-pentyl)-1-hydroxy-2-pyridone stabilizer, compared to an unstabilized sample, shows a distinctly reduced decline in viscosity, and hence significantly increases the stability of the thickener polymer.

Example 6

Hydrogen Peroxide Gel Thickened with a Biopolymer Formulation

| | |
| --- | --- |
| Water, demineralized | ad 100% by wt. |
| Hydrogen peroxide solution (Solvay, 35% by wt., aqueous) | 17% by wt. |
| Hydroxyethyl cellulose | 2.0% by wt. |
| 4-Methyl-6-(2,4,4-trimethylpentyl)-1-hydroxy-2-pyridone | 0.00081% by wt. |

The formulation was produced by dissolving the polymeric thickener in water and then mixing in the hydrogen peroxide solution. The respective start pH was subsequently established with 10% by weight aqueous phosphoric acid. The formulation was produced in each case with and without addition of 8.1 ppm (0.00081% by wt.) of 4-methyl-6-(2,4,4-trimethyl pentyl)-1-hydroxy-2-pyridone.

For this purpose, 10 ml of a 0.1% by weight solution of the stabilizer in propylene glycol were dissolved in 1 liter of water and this solution was used as the water phase. A blank test with propylene glycol ruled out any influence of the solvent. The results of the viscosity measurements are shown in table 6.

TABLE 6

Results of viscosity measurements

| Start pH | 8.1 ppm (=0.00081% by wt.) of 4-methyl-6-(2,4,4-trimethyl-pentyl)-1-hydroxy-2-pyridone | Viscosity [mPa · s] after 10 hours | Viscosity [mPa · s] after 4 weeks 40° C. |
| --- | --- | --- | --- |
| 4.0 | no | 530 | 10 |
| 3.0 | no | 575 | 10 |
| 4.0 | yes | 9850 | 5200 |
| 3.0 | yes | 9800 | 4360 |

At the same time, the hydrogen peroxide content was determined iodometrically in each case. Over the entire storage time, this remained virtually constant at 5.8-6.3% by weight.

The test result shows that the addition of the 4-methyl-6-(2,4,4-trimethyl-pentyl)-1-hydroxy-2-pyridone stabilizer, compared to an unstabilized sample, shows a distinctly reduced decline in viscosity, and hence significantly increases the stability of the thickener polymer.

Example 7

Hydrogen Peroxide Gel Thickened with a Polyalkylene Glycol Formulation

| | |
| --- | --- |
| Water, demineralized | ad 100% by wt. |
| Hydrogen peroxide solution (Solvay, 35% by wt., aqueous) | 17% by wt. |
| Polyethylene glycol (Polyox WSR-301, Dow) | 1.75% by wt. |
| 4-Methyl-6-(2,4,4-trimethylpentyl)-1-hydroxy-2-pyridone | 0.00081% by wt. |

The formulation was produced by dissolving the polymeric thickener in water and then mixing in the hydrogen peroxide solution. The respective start pH was subsequently established with 10% by weight aqueous phosphoric acid. The formulation was produced in each case with and without addition of 8.1 ppm (0.00081% by wt.) of 4-methyl-6-(2,4,4-trimethylpentyl)-1-hydroxy-2-pyridone.

For this purpose, 10 ml of a 0.1% by weight solution of the stabilizer in propylene glycol were dissolved in 1 liter of water and this solution was used as the water phase. A blank test with propylene glycol ruled out any influence of the solvent. The results of the viscosity measurements are shown in table 7.

TABLE 7

Results of viscosity measurements

| Start pH | 8.1 ppm (=0.00081% by wt.) of 4-methyl-6-(2,4,4-trimethyl-pentyl)-1-hydroxy-2-pyridone | Viscosity [mPa · s] immediate | Viscosity [mPa · s] after 1 week 25° C. |
|---|---|---|---|
| 4.0 | no | 2560 | 50 |
| 3.0 | no | 2490 | 60 |
| 4.0 | yes | 2920 | 2100 |
| 3.0 | yes | 3080 | 2050 |

At the same time, the hydrogen peroxide content was determined iodometrically in each case. Over the entire storage time, this remained virtually constant at 5.8-6.3% by weight.

The test result shows that the addition of the 4-methyl-6-(2,4,4-trimethyl-pentyl)-1-hydroxy-2-pyridone stabilizer, compared to an unstabilized sample, shows a distinctly reduced decline in viscosity, and hence significantly increases the stability of the thickener polymer.

Example 8

Hydrogen Peroxide Gel Thickened with a Sulfonate Copolymer Formulation

| | |
|---|---|
| Water, demineralized | ad 100% by wt. |
| Hydrogen peroxide solution (Solvay, 35% by wt., aqueous) | 17% by wt. |
| Aristoflex ® HMS Ammonium Acryloyldimethyltaurate/Steareth-25 Crosspolymer | 0.5% by wt. |
| 4-Methyl-6-(2,4,4-trimethylpentyl)-1-hydroxy-2-pyridone | 0.00081% by wt. |

The formulation was produced by dissolving the polymeric thickener in water and then mixing in the hydrogen peroxide solution. The respective start pH was subsequently established with 10% by weight aqueous phosphoric acid. The formulation was produced in each case with and without addition of 8.1 ppm (0.00081% by wt.) of 4-methyl-6-(2,4,4-trimethylpentyl)-1-hydroxy-2-pyridone.

For this purpose, 10 ml of a 0.1% by weight solution of the stabilizer in propylene glycol were dissolved in 1 liter of water and this solution was used as the water phase. A blank test with propylene glycol ruled out any influence of the solvent. The results of the viscosity measurements are shown in table 8.

TABLE 8

Results of viscosity measurements

| Start pH | 8.1 ppm (=0.00081% by wt.) of 4-methyl-6-(2,4,4-trimethyl-pentyl)-1-hydroxy-2-pyridone | Viscosity [mPa · s] immediate | Viscosity [mPa · s] after 8 weeks 40° C. |
|---|---|---|---|
| 4.0 | no | 3320 | 205 |
| 3.0 | no | 2760 | 745 |
| 4.0 | yes | 3350 | 6100 |
| 3.0 | yes | 2740 | 6000 |

At the same time, the hydrogen peroxide content was determined iodometrically in each case. Over the entire storage time, this remained virtually constant at 5.8-6.3% by weight.

The test result shows that the addition of the 4-methyl-6-(2,4,4-trimethyl-pentyl)-1-hydroxy-2-pyridone stabilizer, compared to an unstabilized sample, shows a distinctly reduced decline in viscosity, and hence significantly increases the stability of the thickener polymer.

Example 9

Hydrogen Peroxide Gel Thickened with a Sulfonate Polymer

Formulation:

| | |
|---|---|
| Water, demineralized | ad 100% by wt. |
| Hydrogen peroxide solution (Solvay, 35% by wt., aqueous) | 17% by wt. |
| Aristoflex ® AVS Sodium Acryloyldimethyltaurate/VP Crosspolymer | 1.0% by wt. |
| 4-Methyl-6-(2,4,4-trimethylpentyl)-1-hydroxy-2-pyridone | 0.00081% by wt. |

The formulation was produced by dissolving the polymeric thickener in water and then mixing in the hydrogen peroxide solution. The respective start pH was subsequently established with 10% by weight aqueous sodium hydroxide. The formulation was produced in each case with and without addition of 8.1 ppm (0.00081% by wt.) of 4-methyl-6-(2,4,4-trimethylpentyl)-1-hydroxy-2-pyridone.

For this purpose, 10 ml of a 0.1% by weight solution of the stabilizer in propylene glycol were dissolved in 1 liter of water and this solution was used as the water phase. A blank test with propylene glycol ruled out any influence of the solvent. The results of the viscosity measurements are shown in table 9.

TABLE 9

Results of viscosity measurements

| Start pH | 8.1 ppm (=0.00081% by wt.) of 4-methyl-6-(2,4,4-trimethyl-pentyl)-1-hydroxy-2-pyridone | Viscosity [mPa · s] immediate | Viscosity [mPa · s] after 2 weeks 25° C. |
|---|---|---|---|
| 9.0 | no | 4450 | 10 |
| 9.0 | yes | 6550 | 7300 |

At the same time, the hydrogen peroxide content was determined iodometrically in each case. From the start value of 6.0% by weight, the hydrogen peroxide content of the solution without stabilizer fell to 0.4% by weight, whereas, with stabilizer, the starting value of 6.0% by weight was maintained.

The test result shows that the addition of the 4-methyl-6-(2,4,4-trimethyl-pentyl)-1-hydroxy-2-pyridone stabilizer, compared to an unstabilized sample, shows a distinctly reduced decline in viscosity, even at high pH, and hence significantly increases the stability of the thickener polymer.

Example 10

Hydrogen Peroxide Gel Thickened with a Sulfonate Copolymer

Formulation:

| | |
|---|---|
| Water, demineralized | ad 100% by wt. |
| Hydrogen peroxide solution | 17% by wt. |
| (Solvay, 35% by wt., aqueous) | |
| Hostapur ® SAS (100% active) | 4.5% by wt. |
| Sodium C14-17 Alkyl Sec Sulfonate | |
| Aristoflex ® TAC | 1.5% by wt. |
| Ammonium Acryloyl Dimethyltaurate/ | |
| Carboxyethyl Acrylate Crosspolymer) | |
| 4-Methyl-6-(2,4,4-trimethylpentyl)-1-hydroxy-2-pyridone | 0.00088% by wt. |

The formulation was produced by dissolving the polymeric thickener in water and then mixing in the hydrogen peroxide solution. The respective start pH was subsequently established with 10% by weight aqueous phosphoric acid. The formulation was produced in each case with and without addition of 8.8 ppm (0.00088% by wt.) of 4-methyl-6-(2,4,4-trimethylpentyl)-1-hydroxy-2-pyridone.

For this purpose, 10 ml of a 0.1% by weight solution of the stabilizer in propylene glycol were dissolved in 1 liter of water and this solution was used as the water phase. A blank test with propylene glycol ruled out any influence of the solvent. The results of the viscosity measurements are shown in table 10.

TABLE 10

Results of viscosity measurements

| Start pH | 8.8 ppm of 4-methyl-6-(2,4,4-trimethyl-pentyl)-1-hydroxy-2-pyridone | Viscosity [mPa · s] immediate | Viscosity [mPa · s] after 4 weeks 40° C. |
|---|---|---|---|
| 4.0 | no | 1340 | 375 |
| 7.0 | no | 1450 | 625 |
| 4.0 | yes | 1320 | 1230 |
| 7.0 | yes | 1400 | 1150 |

At the same time, the hydrogen peroxide content was determined iodometrically in each case. Over the entire storage time, this remained virtually constant at 5.8-6.3% by weight.

The test result shows that the addition of the 4-methyl-6-(2,4,4-trimethyl-pentyl)-1-hydroxy-2-pyridone stabilizer, compared to an unstabilized sample, shows a distinctly reduced decline in viscosity, and hence significantly increases the stability of the thickener polymer.

Formulation Examples

Formulation Example 1

Emulsifier-Containing Bleaching Cream

| Phase | Ingredient | % by wt. |
|---|---|---|
| A | Montanov ® 68 | 1.5 |
| | Cetearyl Alcohol and Cetearyl Glucoside | |
| | Sepinov ® EMT 10 | 1.5 |
| | Hydroxyethyl Acrylate/Sodium Acryloyldimethyl Taurate Copolymer | |
| | Paraffin Oil | 20 |
| B | Sodium Pyrophosphate | 0.6 |
| | Hydrogen peroxide (30% by wt., aqueous) | 6 |
| | Preservative | qs |
| | 4-Methyl-6-(2,4,4-trimethylpentyl)-1-hydroxy-2-pyridone, monoethanolamine salt (Octopirox ®, Clariant) | 0.002 |
| | Water | ad 100 |

Production:

Sepinov EMT 10 is dispersed in phase A. The components of phase B are mixed and phase A is stirred in, forming an emulsion.

Formulation Example 2

Emulsifier-Free Bleaching Gel

| Ingredient | % by wt. |
|---|---|
| Aristoflex ® AVS | 1.0 |
| Sodium Acryloyldimethyltaurate/VP Crosspolymer | |
| Hydrogen peroxide (35% by wt., aqueous) | 17 |
| Sodium pyrophosphate | 0.02 |
| Sodium stannate | 0.04 |
| 4-Methyl-6-(2,4,4-trimethylpentyl)-1-hydroxy-2-pyridone | 0.001 |
| Propylene glycol | 1 |
| Water | ad 100 |

Production:

4-Methyl-6-(2,4,4-trimethylpentyl)-1-hydroxy-2-pyridone is dissolved in propylene glycol. Aristoflex® AVS is dissolved in water, then the hydrogen peroxide solution is stirred in, followed by the two stabilizers.

Formulation Example 3

Oxidative Hair Coloring Formulation

Color Base:

| Ingredient | % by wt. |
|---|---|
| Polyquaternium-29 | 0.5 |
| (Dihydroxypropyl Chitosan Trimonium Chloride) | |
| m-Phenylenediamine | 0.08 |
| p-Phenylenediamine HCl | 0.30 |
| Resorcinol | 0.25 |
| Sodium Bisulfite | 0.30 |
| Sodium Laureth Sulfate | 3.50 |
| Cetyl Alcohol | 15.00 |
| Ammonia, 25% by wt., aqueous | 2.00 |
| Water | ad 100 |

Production:

Cetyl alcohol and sodium laureth sulfate are heated to 60° C., mixed and introduced while stirring into the water phase in which the other constituents have been dissolved.

Developer Gel:

| Ingredient | % by wt. |
|---|---|
| Aristoflex ® TAC Ammonium Acryloyldimethyltaurate/Carboxyethyl Acrylate Crosspolymer | 1.5 |
| Hydrogen peroxide (35% by wt., aqueous) | 18 |
| Sodium pyrophosphate | 0.02 |
| 4-Methyl-6-(cyclohexyl)-1-hydroxy-2-pyridone | 0.002 |
| Propylene glycol | 1 |
| Water | ad 100 |

Production:

4-Methyl-6-(cyclohexyl)-1-hydroxy-2-pyridone is dissolved in propylene glycol. Aristoflex® TAC is dissolved in water, then the hydrogen peroxide solution is stirred in, followed by the sodium pyrophosphate stabilizer.

This forms a gel having a viscosity of approx. 3000 mPa·s at 20° C.

Coloring Procedure:

50 ml of the color base are stirred with 50 ml of the developer gel and applied to the hair. After 30 minutes, it is rinsed out.

Formulation Example 4

Oxidative Hair Coloring Formulation, Ammonia-Free

Color Base:

| Ingredient | % by wt. |
|---|---|
| Polyquaternium-29 (Dihydroxypropyl Chitosan Trimonium Chloride) | 0.5 |
| m-Phenylenediamine | 0.08 |
| p-Phenylenediamine HCl | 0.30 |
| Resorcinol | 0.25 |
| Sodium Bisulfite | 0.30 |
| Sodium Laureth Sulfate | 3.50 |
| Cetyl Alcohol | 15.00 |
| Monoethanolamine | 2.00 |
| Water | ad 100 |

Production:

Cetyl alcohol and sodium laureth sulfate are heated to 60° C., mixed and introduced while stirring into the water phase in which the other constituents have been dissolved.

Developer Gel:

| Ingredient | % by wt. |
|---|---|
| Aristoflex ® TAC Ammonium Acryloyldimethyltaurate/Carboxyethyl Acrylate Crosspolymer | 1.5 |
| Hydrogen peroxide (35% by wt., aqueous) | 18 |
| Sodium pyrophosphate | 0.02 |
| 4-Methyl-6-(2,4,4-trimethylpentyl)-1-hydroxy-2-pyridone | 0.002 |
| Propylene glycol | 1 |
| Water | ad 100 |

Production:

4-Methyl-6-(2,4,4-trimethylpentyl)-1-hydroxy-2-pyridone is dissolved in propylene glycol. Aristoflex® TAC is dissolved in water, then the hydrogen peroxide solution is stirred in, followed by the sodium pyrophosphate stabilizer.

This forms a gel having a viscosity of approx. 3000 mPa·s at 20° C.

Coloring Procedure:

50 ml of the color base are stirred with 50 ml of the developer ael and applied to the hair. It is rinsed out after 30 minutes.

Formulation Example 5

Fixing Gel for Permanent Waves

| Ingredient | % by wt. |
|---|---|
| Aristoflex ® TAC Ammonium Acryloyldimethyltaurate/Carboxyethyl Acrylate Crosspolymer | 0.5 |
| Hydrogen peroxide (35% by wt., aqueous) | 5 |
| Sodium pyrophosphate | 0.02 |
| 4-Methyl-6-(2,4,4-trimethylpentyl)-1-hydroxy-2-pyridone | 0.002 |
| Propylene glycol | 1 |
| Water | ad 100 |

Production:

4-Methyl-6-(2,4,4-trimethylpentyl)-1-hydroxy-2-pyridone is dissolved in propylene glycol.

Aristoflex® TAC is dissolved in water, the hydrogen peroxide solution and the pyrophosphate, and also the propylene glycol solution, are introduced and the mixture is homogenized.

Formulation Example 6

Fixing Gel for Permanent Waves

| Ingredient | % by wt. |
|---|---|
| Aristoflex ® TAC Ammonium Acryloyldimethyltaurate/Carboxyethyl Acrylate Crosspolymer | 0.5 |
| Hydrogen peroxide (35% by wt., aqueous) | 5 |
| Sodium pyrophosphate | 0.02 |
| Polyquaternium-10 (Polymer IR-400) | 0.1 |
| 4-Methyl-6-(2,4,4-trimethylpentyl)-1-hydroxy-2-pyridone | 0.0005 |
| Propylene glycol | 1 |
| Water | ad 100 |

Production:

4-Methyl-6-(2,4,4-trimethylpentyl)-1-hydroxy-2-pyridone is dissolved in propylene glycol.

Polyquaternium-10 is dissolved in water, then Aristoflex® TAC is added while stirring, the hydrogen peroxide solution and the pyrophosphate, and also the propylene glycol solution, are introduced and the mixture is homogenized.

Formulation Example 7

Prewash Spray for Laundry

| Ingredient | % by wt. |
|---|---|
| Aristoflex ® TAC Ammonium Acryloyldimethyltaurate/Carboxyethyl Acrylate Crosspolymer | 0.5 |
| Hydrogen peroxide (35% by wt., aqueous) | 10 |
| Laureth-7 | 5 |
| Laureth-3 | 2 |
| Hostapur ® SAS 60 (Sodium C14-17 Alkyl Sec Sulfonate) | 5 |
| 4-Methyl-6-(2,4,4-trimethylpentyl)-1-hydroxy-2-pyridone | 0.0005 |

-continued

| Ingredient | % by wt. |
|---|---|
| Propylene glycol | 1 |
| Water | ad 100 |

Production:

4-Methyl-6-(2,4,4-trimethylpentyl)-1-hydroxy-2-pyridone is dissolved in propylene glycol.

The surfactants are dissolved in water, then Aristoflex® TAC is added while stirring, the hydrogen peroxide solution and the propylene glycol solution are introduced, and the mixture is homogenized. The product is adjusted to pH=4.

Formulation Example 8

Stain Remover

| Ingredient | % by wt. |
|---|---|
| Aristoflex ® TAC Ammonium Acryloyldimethyltaurate/Carboxyethyl Acrylate Crosspolymer | 0.5 |
| Hydrogen peroxide (35% by wt., aqueous) | 10 |
| Sodium C12-14 Olefin Sulfonate | 5 |
| 4-Methyl-6-(2,4,4-trimethylpentyl)-1-hydroxy-2-pyridone | 0.0005 |
| Propylene glycol | 1 |
| Water | ad 100 |

Production:

4-Methyl-6-(2,4,4-trimethylpentyl)-1-hydroxy-2-pyridone is dissolved in propylene glycol.

The surfactant is dissolved in water, then Aristoflex® TAC is added while stirring, the hydrogen peroxide solution and the propylene glycol solution are introduced, and the mixture is homogenized. The product is adjusted to pH=7.

Formulation Example 9

Stain Remover Gel

| Ingredient | % by wt. |
|---|---|
| Aristoflex ® TAC Ammonium Acryloyldimethyltaurate/Carboxyethyl Acrylate Crosspolymer | 0.5 |
| Hydrogen peroxide (35% by wt., aqueous) | 10 |
| C12/14 Pareth-7 | 7 |
| 4-Methyl-6-(2,4,4-trimethylpentyl)-1-hydroxy-2-pyridone | 0.0005 |
| Propylene glycol | 1 |
| MEA dodecylbenzenesulfonate | 6 |
| Water | ad 100 |

Production:

4-Methyl-6-(2,4,4-trimethylpentyl)-1-hydroxy-2-pyridone is dissolved in propylene glycol.

The surfactants are dissolved in water, then Aristoflex® TAC is added while stirring, the hydrogen peroxide solution and the propylene glycol solution are introduced, and the mixture is homogenized. The product is adjusted to pH=4.7.

The invention claimed is:

1. A composition comprising
   a) 1% to 10% by weight of at least one substance selected from the group consisting of hydrogen peroxide and hydrogen peroxide-releasing substances;
   b) water;
   c) at least one polymer having at least one thickening property and having a molecular weight of more than 5000 g/mol; and
   d) 0.5 to 1000 ppm of at least one substance selected from the group consisting of compounds of the formula (I) and salts thereof

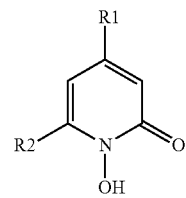

(I)

in which R1 is H or a $C_1$-$C_4$ alkyl radical and R2 is H, an unsubstituted or halogen-substituted, branched or unbranched $C_1$-$C_{20}$ alkyl radical, an unsubstituted or halogen-substituted $C_5$-$C_8$ cycloalkyl radical, an unsubstituted or halogen-substituted $C_6$-$C_{10}$ aryl radical or an unsubstituted or halogen-substituted, branched or unbranched $C_7$-$C_{20}$ aralkyl radical;
wherein the viscosity of the composition is 50 to 100000 mPa·s at 20° C., and wherein the pH of the composition is in the range of 2-7, and wherein the substance selected from the group consisting of compounds of the formula (I) and salts thereof is present in an amount such that the composition exhibits a viscosity stability over 4 weeks from formulation at 40° C. of at least 68%.

2. The composition as claimed in claim 1, wherein the at least one substance of component a) is selected from the group consisting of hydrogen peroxide, urea peroxide, perborates, persulfates and mixtures thereof.

3. The composition as claimed in claim 1, wherein the substance of component a) is hydrogen peroxide.

4. The composition as claimed in claim 1, wherein the at least one polymer having at least one thickening property of component c) is selected from the group consisting of polymers having a C—C backbone, biopolymers, modified biopolymers, associative thickeners and polyalkylene glycols.

5. The composition as claimed in claim 4, wherein the at least one polymer having at least one thickening property of component c) is selected from the group consisting of polymers having a C—C backbone.

6. The composition as claimed in claim 5, wherein the at least one polymer having a C—C backbone is a partly or fully neutralized polymer containing sulfo groups.

7. The composition as claimed in claim 6, wherein the at least one partly or fully neutralized polymer containing sulfo groups is selected from the group consisting of homo- or copolymers of acrylamidomethylpropanesulfonic acid and salts thereof.

8. The composition as claimed in claim 4, wherein the at least one polymer having at least one thickening property of component c) is selected from the group consisting of biopolymers and modified biopolymers.

9. The composition as claimed in claim 4, wherein the at least one polymer having at least one thickening property of component c) is selected from the group consisting of associative thickeners.

10. The composition as claimed in claim 9, wherein the at least one associative thickener is selected from the group consisting of phosphoric esters.

11. The composition as claimed in claim 4, wherein the at least one polymer having at least one thickening property of component c) is selected from the group consisting of polyalkylene glycols.

12. The composition as claimed in claim 1, wherein the at least one compound of component d) is present in the form of the acid or in the form of the alkali metal, alkaline earth metal or amine salt thereof or a salt thereof with a polymeric counterion.

13. The composition as claimed in claim 1, wherein, in the at least one compound of the formula (I) or in the salt thereof, R1 is methyl and R2 is cyclohexyl or 2,4,4-trimethylpentyl.

14. The composition as claimed in claim 1, wherein R1 and R2 in the at least one compound of the formula (I) or in the salt thereof are each H.

15. The composition as claimed in claim 1, which comprises the at least one substance of component d) in an amount of 0.1 ppm to 2% by weight, based on the total weight of the composition.

16. The composition as claimed in claim 1, which has a pH of 2.5-4.5.

17. A composition for bleaching and/or coloring of hair or a permanent wave formulation, comprising at least one composition according to claim 1.

18. An oxidative cleanser formulation, comprising at least one composition according to claim 1.

19. A stain removal gel for pretreatment of laundry, a prewash spray, a stain remover, a surface cleaner, a toilet cleaner, a multifunctional stain removal gel or a bleaching gel, comprising at least one composition according to claim 1.

20. A method for stabilization of at least one polymer having at least one thickening property in a composition as claimed in claim 1, comprising the step of adding at least one substance selected from the group consisting of compounds of the formula (I) and salts thereof to the composition.

21. The method as claimed in claim 20, wherein the at least one polymer having at least one thickening property is a partly or fully neutralized polymers containing sulfo groups.

22. The method as claimed in claim 21, wherein the at least one partly or fully neutralized polymers containing sulfo groups are selected from the group consisting of homo- or copolymers of acrylamidomethylpropanesulfonic acid and salt thereof.

23. A composition according to claim 1, in the form of a bleach composition for hair, a developer for a hair dye, or a permanent wave formulation.

24. A composition according to claim 1, in the form of a bleach composition for teeth or a household cleaner.

25. A composition according to claim 1, having wherein the viscosity of the composition is 150 to 5000 mPa·s at 20° C.

26. A composition comprising
a) 1% to 10% by weight of at least one substance selected from the group consisting of hydrogen peroxide and hydrogen peroxide-releasing substances;
b) water;
c) at least one polymer having at least one thickening property and having a molecular weight of more than 5000 g/mol; and
d) 0.5 to 1000 ppm of at least one substance selected from the group consisting of compounds of the formula (I) and salts thereof

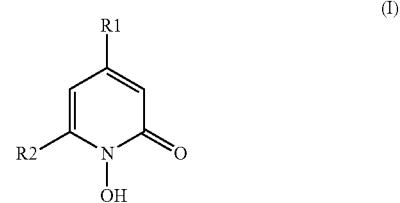

in which R1 is H or a $C_1$-$C_4$ alkyl radical and R2 is H, an unsubstituted or halogen-substituted, branched or unbranched $C_1$-$C_{20}$ alkyl radical, an unsubstituted or halogen-substituted $C_5$-$C_8$ cycloalkyl radical, an unsubstituted or halogen-substituted $C_6$-$C_{10}$ aryl radical or an unsubstituted or halogen-substituted, branched or unbranched $C_7$-$C_{20}$ aralkyl radical, the at least one substance being present in an amount to stabilize the viscosity of the composition relative to an identical composition lacking the at least one substance;
wherein the viscosity of the composition is 50 to 100000 mPa·s at 20° C., and wherein the pH of the composition is in the range of 2-7, and wherein the substance selected from the group consisting of compounds of the formula (I) and salts thereof is present in an amount such that the composition exhibits a viscosity stability over 4 weeks from formulation at 40° C. of at least 68%.

* * * * *